United States Patent
Grupp

(10) Patent No.: US 11,219,734 B2
(45) Date of Patent: Jan. 11, 2022

(54) VENTILATOR SYSTEM WITH REMOVABLE AIRWAY

(71) Applicant: LifeAir, LLC, Portland, OR (US)

(72) Inventor: Daniel Grupp, Portland, OR (US)

(73) Assignee: LIFEAIR, LLC, Portland, OR (US)

(*) Notice: Subject to any disclaimer, the term of this patent is extended or adjusted under 35 U.S.C. 154(b) by 0 days.

(21) Appl. No.: 17/241,248

(22) Filed: Apr. 27, 2021

(65) Prior Publication Data
US 2021/0338966 A1   Nov. 4, 2021

Related U.S. Application Data

(60) Provisional application No. 63/016,995, filed on Apr. 29, 2020, provisional application No. 63/086,055, filed on Oct. 1, 2020, provisional application No. 63/086,375, filed on Oct. 1, 2020.

(51) Int. Cl.
*A61M 16/20* (2006.01)
*A61M 16/08* (2006.01)
*A61M 16/00* (2006.01)

(52) U.S. Cl.
CPC .... *A61M 16/0875* (2013.01); *A61M 16/0057* (2013.01); *A61M 16/20* (2013.01); *A61M 2016/003* (2013.01); *A61M 2016/0027* (2013.01); *A61M 2205/52* (2013.01); *A61M 2250/00* (2013.01)

(58) Field of Classification Search
CPC ....... A61B 5/0813; A61B 5/083; A61B 5/097; A61M 16/0057; A61M 16/0875; A61M 16/20; A61M 2016/0027; A61M 2016/003; A61M 2205/52; A61M 2250/00; Y10S 128/914; Y10T 137/877; Y10T 137/87893
See application file for complete search history.

(56) References Cited

U.S. PATENT DOCUMENTS

| | | | |
|---|---|---|---|
| 3,229,509 A | 1/1966 | Darby | |
| 3,901,230 A | 8/1975 | Henkin | |
| 4,991,576 A | 2/1991 | Henkin et al. | |
| 5,119,825 A * | 6/1992 | Huhn | A61B 5/083 128/205.17 |

(Continued)

OTHER PUBLICATIONS

International Search Report dated Aug. 18, 2021 from International Application No. PCT/US2021/029428, 9 pgs.

(Continued)

*Primary Examiner* — Annette Dixon
(74) *Attorney, Agent, or Firm* — Jackrel Consulting, Inc.; David Jackrel

(57) ABSTRACT

The present disclosure provides techniques for a ventilator system with a removable airway. A ventilator system may include a removable airway and a base unit. The removable airway may include an air inlet port, a patient inhalation port, an air exhaust port, a patient exhalation port, a first portion of a pressure sensor, and a first portion of a flow sensor. The base unit may include two pinch valves, a second portion of the pressure sensor, and a second portion of the flow sensor. In some cases, the airway does not comprise any openings other than the air inlet port, the air exhaust port, the patient inhalation port, and the patient exhalation port. In some cases, air inside the removable airway does not contact any part of the base unit without first exiting the air exhaust port.

20 Claims, 19 Drawing Sheets

(56) References Cited

U.S. PATENT DOCUMENTS

| | | | |
|---|---|---|---|
| 5,303,712 A * | 4/1994 | Van Duren | A61B 5/0813 |
| | | | 600/529 |
| 5,398,675 A | 3/1995 | Henkin et al. | |
| 5,931,162 A | 8/1999 | Christian | |
| 7,562,584 B2 | 7/2009 | Conquergood | |
| 2001/0029340 A1 | 10/2001 | Mault et al. | |
| 2007/0157931 A1 | 7/2007 | Parker et al. | |
| 2012/0191059 A1 | 7/2012 | Cummings et al. | |
| 2016/0235932 A1 | 8/2016 | Rankin | |
| 2017/0254685 A1 | 9/2017 | Wilt et al. | |
| 2017/0266399 A1 | 9/2017 | Campana et al. | |
| 2019/0099578 A1 | 4/2019 | Wolfson et al. | |
| 2019/0142303 A1 | 5/2019 | Wondka et al. | |
| 2020/0121872 A1 | 4/2020 | Grundler et al. | |

OTHER PUBLICATIONS

Written Opinion dated Aug. 18, 2021 from International Application No. PCT/US2021/029428, 4 pgs.

* cited by examiner

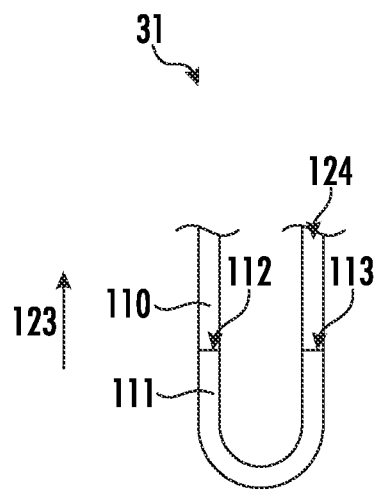
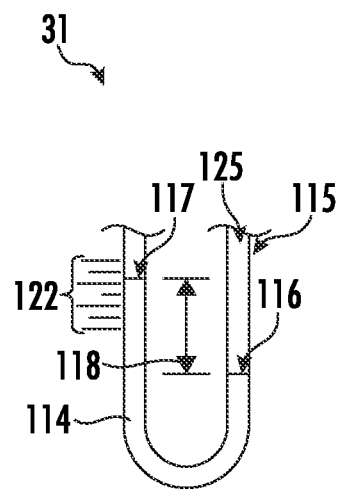
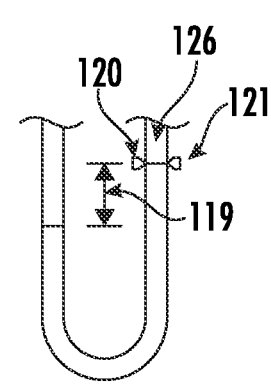
FIG. 13A  FIG. 13B  FIG. 13C
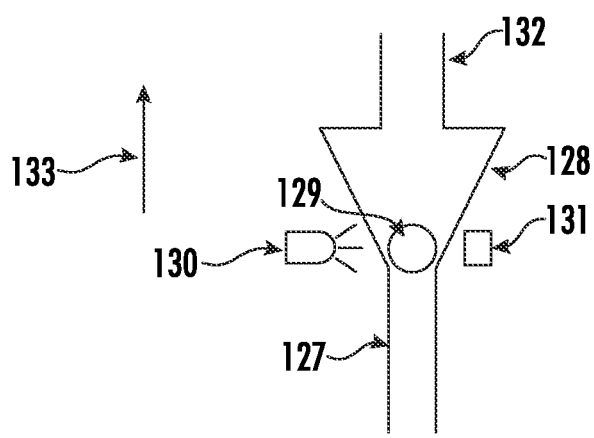
FIG. 14

VENTILATOR SYSTEM WITH REMOVABLE AIRWAY

RELATED APPLICATIONS

This application claims the benefit of: 1) U.S. Provisional Patent Application No. 63/016,995, filed on Apr. 29, 2020, and entitled "Ventilator"; 2) U.S. Provisional Patent Application No. 63/086,055, filed on Oct. 1, 2020, and entitled "Ventilator with Removable Airway"; and 3) U.S. Provisional Patent Application No. 63/086,375, filed on Oct. 1, 2020, and entitled "Ventilator with Removable Airway"; all of which are hereby incorporated by reference for all purposes.

BACKGROUND

A ventilator is a machine that provides mechanical ventilation by moving breathable air into and out of the lungs of a patient, for example, to deliver breaths to a patient who is physically unable to breathe, or is breathing insufficiently. Conventional ventilators may be machines with valves controlled by a computerized (e.g., microprocessor-controlled) control system based on the feedback of sensors (e.g., pressure and flow sensors), or may be more basic machines (e.g., containing a hand-operated bag, a valve, and a mask). Ventilators are typically used in intensive-care medicine, home care, emergency medicine, and in anesthesiology (as a component of an anesthesia machine).

There are different types of conventional ventilators, such as volume ventilators and pressure-cycled ventilators. Conventional ventilators are susceptible to contamination, for example, from a patient coupled to the ventilator. The interior surfaces of the ventilator, including valves and sensors, are exposed to air exhaled from a patient. The air from a patient may contain pathogens, such as bacteria associated with nosocomial pneumonia, which can contaminate the ventilator and potentially infect a subsequent user of the ventilator (e.g., the next patient to use the ventilator). Some components of conventional ventilators may be cleaned or replaced between use by different patients, however, cleaning or replacing some components is ineffective if other adjoining regions within the ventilator remain contaminated. For example, bacteria that remains in some areas of a ventilator (e.g., a moving component of a valve, or a surface of a pressure or flow sensor) may contaminate the air stream moving through the ventilator, thereby contaminating the rest of the system.

SUMMARY

The present disclosure provides techniques for a ventilator system with a removable airway. In some embodiments, a ventilator system includes a removable airway and a base unit (or a base ventilator unit). The removable airway may include an air inlet port, a patient inhalation port, an air exhaust port, a patient exhalation port, a first portion of a pressure sensor, and a first portion of a flow sensor. The base unit may include two pinch valves, a second portion of the pressure sensor, and a second portion of the flow sensor. Air may enter the removable airway through the air inlet port, be exhausted from the removable airway through the air exhaust port, leave the removable airway through the patient inhalation port, and enter the removable airway through the patient exhalation port. In some cases, the airway does not comprise any openings other than the air inlet port, the air exhaust port, the patient inhalation port, and the patient exhalation port. In some cases, air inside the removable airway does not contact any part of the base unit without first exiting the air exhaust port.

In some embodiments, a ventilator system includes a removable airway and a base unit. The removable airway may include four ports comprising an air supply port, an air exhaust port, a patient inhalation port, and a patient exhalation port, a first portion of a first pressure sensor comprising a compliant region, and a first portion of a first flow sensor comprising a diaphragm. The base unit may include two pinch valves, each pinch valve comprising a valve body, an actuator, a moveable element, and a fixed element, wherein the removable airway passes between the fixed element and the moveable element, a second portion of the first pressure sensor comprising a load cell configured to measure a force on the compliant region, and a second portion of the first flow sensor comprising a microphone configured to measure a sound emitted from the diaphragm. In some cases, the removable airway does not comprise any openings other than the four ports. In some cases, air inside the removable airway does not contact any part of the base unit.

In some cases of the ventilator systems described above, the removable airway further includes in inhale manifold and an exhale manifold. The inhale manifold may include the air supply port, the patient inhalation port, the first portion of the first pressure sensor, and the first portion of the first flow sensor. The exhale manifold may include the air exhaust port, the patient exhalation port, a first portion of a second pressure sensor, and a first portion of a second flow sensor. In some cases of the ventilator systems described above, the base unit further includes a first and a second pinch valve configured to limit flow in the inhale manifold, wherein the moveable element of each of the first and second pinch valves comprise a roller coupled to a rotatable arm, a third and a fourth pinch valve configured to limit flow in the exhalation manifold, wherein the moveable element of each of the third and fourth pinch valves comprise a roller coupled to a rotatable arm, the second portion of the first pressure sensor, the second portion of the first flow sensor, a second portion of the second pressure sensor, and a second portion of the second flow sensor.

BRIEF DESCRIPTION OF THE DRAWINGS

FIGS. 13A-13C are simplified schematics of an example of a pressure detection system, in accordance with some embodiments.

FIG. 14 is a simplified schematic of an example of a flow sensor, in accordance with some embodiments.

DETAILED DESCRIPTION

Figure 1:
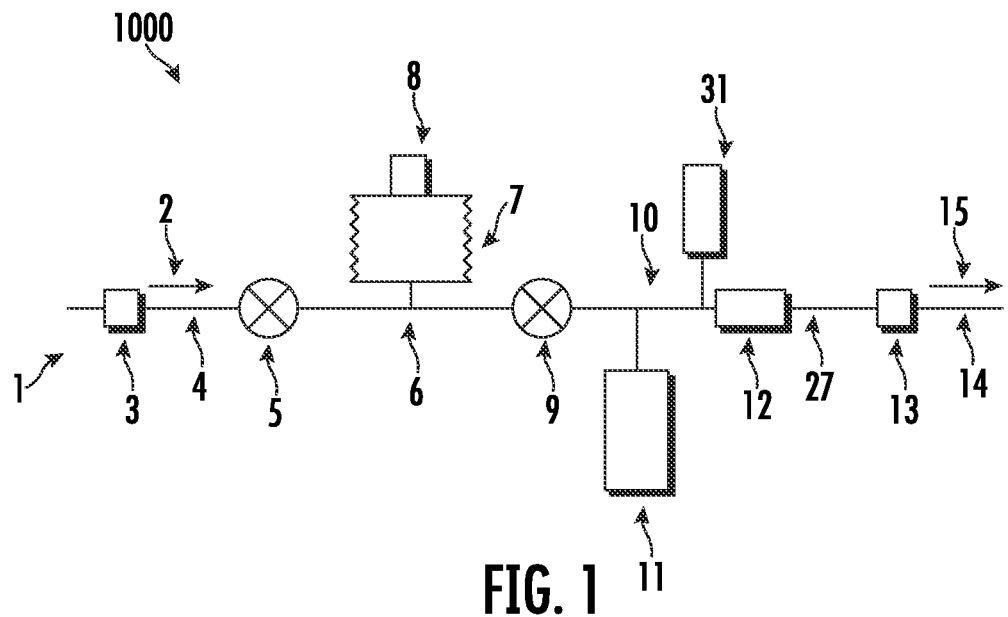
FIG. 1 is a simplified schematic of an example of an inhale manifold of a ventilator system, in accordance with some embodiments.

A ventilator system is disclosed for supporting breathing in a human or other animal, such as a primate. The ventilator system may contain a removable unit and a base unit, where the removable unit may also be disposable.

In some cases, the removable unit can be removed from the base unit manually (e.g., using a person's hands only). In some cases, the removable unit can be removed from the base unit without using any tools (e.g., without using a screwdriver, or pliers, or any other tools). In some cases, the removable unit can be removed from the base unit with a tool (e.g., a screwdriver), wherein the number of operations required to remove the removable unit is minimal, such as from 1 to 4 operations (e.g., where the 1 to 4 operations comprise removing 1 to 4 screws). In some cases, the removable unit may be removed and disposed of periodically (e.g., between use of the ventilator by different patients, or after a particular time duration, such as daily or weekly).

In some cases, all of the air exhaled from a patient coupled to the ventilator (e.g., through a patient circuit, and/or endotracheal tube) is constrained to move within the removable unit (e.g., a removable airway), and/or none of the air exhaled from the patient may contact the base unit. In some cases, the air exhaled from the patient passes through the removable unit, without contacting the base unit, and then air is expelled from a port of the removable unit (e.g., through a filter) into the atmosphere wherein it may contact some portions (e.g., exterior surfaces) of the base unit. Cross-contamination between patients can be eliminated (or mitigated, or reduced) using the ventilators described herein, which include a removable unit (e.g., airway) that 1) may be removed and replaced between patients, and 2) that prevents air (and other materials or particles) exhaled from the patient from contacting any part of the ventilator other than the removable unit (e.g., from contacting any part of the base unit).

The air in the ventilator systems described herein may contain oxygen, nitrogen, other gases, other materials (such as liquid particles, solid particles, pathogens, and/or medicinal aerosols), and mixtures thereof.

In some embodiments, the ventilator systems described herein include valves to control the flow of air through the removable unit. The valves can include moving parts to reduce the flow through a portion (e.g., a tube) of the removable unit. In some cases, no moving parts of the valves come into contact with air exhaled from a patient that is coupled to the ventilators described herein. For example, a valve can contain a moving element and a fixed element, where the moving element is configured to compress a tube of the removable unit (where the tube is positioned between the movable and the fixed element) thereby restricting flow through the tube in a controlled manner.

In some embodiments, the removable airway system may contain a one-way valve that opens at a preset pressure, such as a blow-off valve. The preset pressure may be set at a level that protects the lungs from overpressure, such as 50 or 60 cmH$_2$O. The base unit may have a subsystem for detection of an overpressure event such as detecting motion of the valve or flow from the valve.

In some embodiments, the ventilator systems described herein include sensors (e.g., pressure sensors, flow sensors, and temperature sensors). In some cases, the sensor is contained in the base unit, such that no part of the sensor can come into contact with air exhaled from a patient that is coupled to the ventilators described herein. In other embodiments, the sensor is contained within the removable unit, and may have electrical connections (e.g., wires) that penetrate a portion (e.g., a tube) of the removable unit (e.g., through sealed openings that do not allow air from the removable unit to escape through). In other embodiments, the sensors have a portion in the removable unit and a portion in the base unit, wherein the portion in the removable unit may come into contact with air exhaled from a patient that is coupled to the ventilator, and the portion in the base unit cannot come into contact with air exhaled from a patient that is coupled to the ventilator. For example, a pressure sensor can contain a compliant region (e.g., disposed on a surface of a tube) of the removable unit, and a load cell adjacent to the compliant region in the base unit, such that pressure changes within the removable unit create changes in a force on the compliant region thereby causing the compliant region to move and the load cell to detect the force (and/or movement) of the compliant region. In this example, the compliant region would be exposed to air exhaled from a patient, but the load cell would not come into contact with air exhaled from the patient. Such sensors can be cost effective, since inexpensive portions can be located within the removable unit (e.g., to be disposed of after use by a patient, before the ventilator is used by a different patient), while the more expensive portions (e.g., the load cell in this example) can be protected from contamination and therefore be used many times (e.g., by different patients).

In some cases, the complexity of the removable unit is minimized, for example, to minimize cost of a potentially disposable removable unit.

In some embodiments, the ventilator includes: 1) an airway manifold (i.e., removable airway) that is removable (and in some cases is also disposable), where the removable airway may transfer air exhaled from a patient coupled to the ventilator to a filtered exhaust; 2) a base ventilator unit, where the removable airway and the base unit are configured such that no air from a patient touches any components of the base ventilator unit; 3) valves, including valve components that no air from a patient touches (e.g., using a moving element to compress a tube of the removable airway); 4) pressure sensors that are configured with pressure sensor components that no air from a patient touches (e.g., using a compliant component in the airway and a pressure sensor component outside the airway that no air from a patient touches, or water-based sensors); 5) flow sensors that are configured with flow sensor components that no air from a patient touches (e.g., using a diaphragm component in the airway and a flow sensor component outside the airway that no air from a patient touches); and/or 6) a control system coupled to the valves, that may also be coupled to the sensors, where the control system controls the opening and closing of the valves to control the flow of air through the removable airway. In some cases, a measurement of pressure or flow or volume within the removable airway is converted to an electrical signal via an electric eye.

In some embodiments, the ventilator system is comprised of pressure and flow controlling subsystems (e.g., valves) and measurement components (e.g., sensors). The removable unit (or airway) of the ventilator systems described herein may include an air manifold for incoming air to a patient (i.e., an inhale manifold), and a manifold for air leaving a patient (i.e., an exhale manifold).

The ventilator systems described herein may also include a control system for opening and closing of valves. The control system may be coupled to one or more valves of the ventilator system to control the opening and closing of the valves. The control system may be coupled to one or more sensors, and may be configured to receive signals from the sensors, process the signals into information, and use the information to control one or more components (e.g., one or more valves) of the system. The processor may communicate with the one or more valves, and/or with the one or more sensors, through a bus system. The control system may contain a processor (or microprocessor), and may contain non-transitory computer readable memory coupled to the processor (e.g., through a bus system).

In some cases, the electronics of the system may have no microprocessor. In some cases, all functions may be hard-wired into an analog and/or digital circuit, such that the system has no software. This can be beneficial for safety testing and development cost.

In some embodiments, the removable unit of the ventilators described herein includes connections for air in and air out, and connections to a patient for inhale and exhale lines (e.g., of a patient circuit and/or endotracheal tube). The air that passes through the removable unit may have no pathway, connection, or contact to any part of the base ventilator unit. The air from a patient connected to the ventilator system may not contact any of the base unit. In some cases, the air from a patient connected to the ventilator system may not contact any of the base unit without passing through an exhaust port, which may be filtered. That is, there may be no pathway through open conduits from the airway of a patient connected to the ventilator system and the base unit. In some cases, there may be no pathway through open conduits from the airway of a patient connected to the ventilator system and the base unit that are not filtered exhaust ports. Again, the air or any other particle or matter that can come into the ventilator from tubes or other means connecting to a patient is completely isolated from the rest of the ventilator, meaning there is no way for the air or matter to reach and contact surfaces of the ventilator outside of the removable parts. In some cases, the air or any other particle or matter that can come into the ventilator from tubes or other means connecting to a patient is completely isolated from the rest of the ventilator, and there is no way for the air or matter to reach and contact surfaces of the ventilator outside of the removable parts, other than by exiting an exhaust port first. Regions or surfaces of the base unit that are not intended to be in contact with air within the removable unit are considered outside of the removable unit. The base unit is a part of a ventilator system that is other than the disposable unit or disposable system(s) or subsystem(s).

In some cases, the air from a patient connected to the ventilator system contacts a first removable unit (airway), the patient is disconnected from the ventilator system, and the first removable unit (airway) is removed from the base unit and replaced with a second removable unit (airway). In such cases, the air from the patient may contact the first removable unit (airway), and air from the patient may contact a portion of the base unit, as long as any contamination on the portion of the base unit cannot be introduced into the second removable unit (airway). For example, a patient may contaminate the first removable unit (airway) with bacteria, and the air from the patient may contact a portion of the base unit thereby contaminating that portion of the base unit. However, the contamination from the portion of the base unit cannot contaminate the second removable unit (airway) (e.g., due to positive pressure second within the removable airway). This case could arise in the case that air from the first removable unit (airway) leaks and contaminates the base unit, however, there is no path for the contamination from the base unit to reenter the first or enter the second removable unit (airway) (e.g., due to positive pressure within the second removable airway).

In some cases, air may leak from a connection between the ventilator systems described herein and a patient circuit, and that air could possibly contact a part of the base without exiting through an exhaust port (or a dedicated exhaust port). However, in such cases, air that leaks from the patient connection is not air inside the removable airway.

In some cases, air or matter from a patient within the removable airway passes through one or more filters before leaving an exit port to the atmosphere. In some cases, air or matter from a patient within the removable airway may only leave through one or more openings (e.g., an exit port, or a patient inhale circuit) and the one or more openings are dedicated openings, wherein the dedicated opening is used to expel excess gas from the airway (e.g., to the atmosphere, or to a patient) and the dedicated opening is not used for any other function (e.g., as a sensor port). Additionally, in some cases, all of the valve components used to constrict flow within the removable airway are contained in the base unit, and no valve components can contact the air (or matter contained therein) that is exhaled from the patient. In other cases, the removable unit may have one or more valve components that are portions of the valve system, where the valve components may or may not contact the air within the removable unit. In some cases, the valve components can be coupled to the outside or the inside of the tube of the removable unit that contains the air. For example, the removable unit may contain a valve component that is in contact with the outside of a tube, where the valve component is a first portion of the valve. When such a removable unit is inserted in the base unit, a second portion of the valve in the base unit may push against the valve component (e.g., a plunger) of the first portion of the valve, and the valve component may push against the tube rather than the valve in the base unit pushing against the tube directly.

In some cases, the incoming air that will be supplied to the patient enters the removable airway at a port. A valve may be disposed downstream of the port. The incoming air has a pressure such that when the valve is opened, there is an airflow through the valve downstream, which prevents any matter that may be in the airway downstream of the valve from moving upstream of the valve. In this manner, the source of gas is protected from contamination by patient air or matter.

In some cases, a pathogen (e.g., bacteria) from the environment could contaminate a removable unit (airway) of the ventilator systems described herein, for example, by entering the removable unit through an inlet. The ventilator systems described herein are advantageous in such situations because the removable unit (airway) can be removed periodically (e.g., between patients) thereby limiting the amount of time the pathogen (e.g., bacteria) can grow within the removable unit (airway), and limiting the number of patients exposed to the contamination.

In some cases, the airway is configured to be cleaned in place (e.g., the airway may be configured to be removable and also configured to be cleaned in place, or the airway may not be configured to be removable). The capability to be cleaned may be enabled by the isolation of the airway from the base unit. The systems described herein may be suitable for cleaning due to the lack of tortuous paths and nooks and crannies (or regions which are tightly confined such as cracks or small tubes, where tight and small are defined with respect to the ability of a cleaning agent to penetrate these regions). In some cases, the materials of the airway are suitable for chemical, thermal, or UV sterilization. In some cases, the airway of the ventilators described herein is generally straight and contains no volume regions that are less than 10 mm at their smallest dimension, or spaces that have dimensions (i.e., interior dimension of the space) smaller than 5 mm. The above shapes and sizes of the airway can make the ventilator system described herein easy to clean. In some embodiments, a ventilator system described herein has an isolated airway that is easily cleanable without the need to remove any parts of the system. To clean the ventilator systems described herein sterilizing agent may be introducible by connection to the various inlets and outlets. Other sterilizing methods such as heat and ultraviolet light may also be used to clean the ventilator systems described herein.

The ventilator systems described herein may include airways that are removable from a base unit, and that may be removed to be cleaned or to be disposed of. If disposed of, then they can be subsequently replaced with a new unit or a cleaned unit. In some embodiments, the isolated airway is removable. In some embodiments, the removable airway is disposable. In some embodiments, the removable airway is cleanable. These embodiments are not mutually exclusive.

In some embodiments, ventilator systems described herein include one or more valves that compress a tube that passes through the valve. Such valves are commonly called "pinch" valves. In a pinch valve, the tube may be removed from the valve. Pinch valves have the preferred advantage that no fluid from inside the tube touches the valve components. Thus, no sterilization of the valve is needed between uses if the tube is removed and disposed of and another tube is inserted into the valve. In some cases, a pinch valve of a ventilator described herein has an open position (or tube removal position) that allows insertion and removal of the tube. In some cases, the valve has an open position used during operation, and a tube removal position where the valve opens wider than in the open position.

In some cases, the pinch valves of the ventilator systems described herein may be configured to variably adjust the flow of gas through the valve (i.e., through a tube passing through the valve, or through a compressible section of a tube passing through the valve). By varying the pressure on the tube that passes through the pinch valve, the amount of compression in a region of the tube may be varied from no compression, to partially compressed, to fully compressed. When the tube has no compression, the valve is in a fully open position, where the flow through the valve is maximal. When the region of the tube is fully compressed, the cross-sectional area of an interior space of the tube where it is compressed is zero, so no air may pass through the tube, and the valve is considered fully closed. In a partially compressed position, the cross-sectional area of the interior space of the tube at the region of compression is reduced compared to the fully open position, resulting in higher flow resistance, with an associated reduced flow when gas is passing through the valve. The moveable component of the valve may in some cases have a continuously or nearly continuously adjustable range of positions which result in a continuous or nearly continuous range of cross-sectional areas of an interior space of the tube. In this manner, the flow rate of the pinch valve with a tubing section of the removable airway passing through it may be continuously or nearly continuously adjusted.

In some cases, a pinch valve of the ventilator systems described herein that can variably adjust the flow of gas through the valve, includes a rotating arm that is controlled by a stepper motor to adjust the flow through the valve. The steps of the stepper motor may be miniscule, such as 0.1 degrees per step, such that there is a minimum of adjustment size, where in some cases this minimum level of motion results in changes of flow below the level of detection of flow sensors of the system. This case may be considered as an example of a valve that can be nearly continuously adjusted.

A pinch valve of the ventilator systems described herein that can variably adjust the flow of gas through the valve may also have a set of predetermined positions or settings such that the flow may be varied over a set of values, such as 0, ¼, ½, ¾ and 1 where these numbers correspond to the fraction of flow through the valve compared to a full flow through the valve.

A pinch valve of the ventilator systems described herein that can variably adjust the flow of gas through the valve may be configured in some cases in either open loop or closed loop control. In open loop control, the valve may be set at positions determined by predetermined settings, and not at positions determined as a result of sensor readings. In closed loop control, the position of the valve is changed in response to a sensor reading, such as a flow sensor. In some cases, there is a continuing cycle wherein the sensor value is determined by a control system, and this sensor value (e.g., a flow rate) is compared to a setting value (e.g., a flow rate) that has been input to the control system, and a difference is determined. This difference is then used to either further open or close the valve in order to make the difference smaller (i.e., to make the sensor value closer to the setting value). For example, if a measured flow is higher than an input setting, then the valve would be adjusted to a more closed position in response to the measured flow value. After adjustment of the valve, the sensor may then be read again, and the valve further adjusted. The cycle may continue until the difference between the sensor reading and the input setting are the same within system tolerances or a preset minimum difference. The increments by which the valve is adjusted for each cycle may be set in a control algorithm, such as using a Proportional, Integral, Derivative (PID) control method. The control algorithm may also include artificial intelligence (AI) wherein a position needed to achieve a particular flow rate may be derived from a set of past data from a plurality of inputs of the system wherein the valve setting may be learned from the data set.

The ventilator systems disclosed herein may contain a device or subsystem for the generation of a mixed gas with a particular fraction of inspired oxygen ($FiO_2$) (e.g., between about 0.2 and about 1.0, or between 0.21 and 0.5, or between 0.21 and 1.0) from pure oxygen. A gas source may be connected directly to an inlet port of the removable unit. The gas source be a mixed gas with a particular $FiO_2$. The source of the gas may be a pressurized line, a tank, or a compressor or blower. The base unit may have inlets for multiple gas sources, such as oxygen and nitrogen, and the base unit may have a subsystem for blending these inlet gases, and an outlet that provides the mixed gases to the input of the removable unit.

In some cases, pinch valves with rotary elements for the ventilator systems herein can use motors with 30 RPM and a torque of 40 gram-cm. For example, such a motor can be used to compress a silicone tube (e.g., with a ½" diameter).

The removable unit (airway) may contain one or more tubes. The tubes in the ventilator systems described herein may be of any flexible material such as vinyl or silicone. In some cases, the tube can withstand multiple (e.g., about 1 million, or from 100,000 to 2 million, or from 100,000 to 10 million, or more than 1 million, or more than 10 million) compression (or inhale, or exhale) cycles. For example, breathing at 20 breaths/minute for 10 days is 288,000 cycles. Vinyl and silicone are examples of tubing material that can meet the requirements of the ventilator systems described herein. In some cases, the tubing may contain reinforcement fibers within or connected to the tubing walls, such that the tubing may withstand higher pressures than without the reinforcement fibers, yet remain compressible. In some cases, the removable unit (or airway) may be made of low cost plastic materials so that it is not costly to dispose of between patients.

The motor used by the valves in the ventilator systems described herein may be any motor capable of actuating the valve, or providing movement for a component of the ventilator system such as a DC motor, a stepper motor, a servo motor, a controllable positionable motor, a linear actuator, or a positionable actuator. A control circuit may position the motor by turning it on and off. In some cases, the position of the motor may be determined by an electric eye, including a light emitter and a light sensor.

The removable system of the ventilators described herein may contain sensors. Sensors may be for pressure, flow, and/or other parameters (e.g., temperature). The sensors may be active, such as powered by electricity. If the removable system contains sensors, then the removable system may have connectors on the removable system that mate to connectors on the base unit of the ventilators described herein. The connectors may be electrical. Electrical connections to sensors in the ventilators described herein may also be non-contact. Power to the sensors may be wireless, such as using the Qi standard, or other radiative or inductive means. Communication with the processor or control system (e.g., from a sensor, and/or to a valve) of the ventilators described herein may be wireless or wired, such as by WiFi or Bluetooth.

The removable unit of the ventilators described herein may have regions or systems that together with a related system in the base unit form a sensor system. In some embodiments, the regions or systems in the removable unit are passive, in that they do not contain any active components, such as electronics or sensors that receive electrical power.

In some cases, the ventilator systems described herein use electric eyes containing an emitter and a detector configured to detect one or more conditions within the system. The electric eyes disclosed herein may be configured with the emitter and the detector on either side of a (transparent, or translucent) region of interest (e.g., a tube). In other cases, the emitter and detector can be configured such that light from the emitter reflects off of a reflective surface, such as a retroreflective surface, or a high contrast light and dark surface, and is detected by the detector. For example, the emitter and the detector may be facing generally the same direction and be close to, or within a proximity of, each other.

In some cases, the ventilator systems described herein have parameters that are adjustable either electrically or mechanically. For example, the delays between cycles which are related to the inhale:exhale time ratio, may be adjusted by an input to a control system such as with a knob and a variable resistor. Peak inspiratory pressure (PIP) may be adjusted, for example, by moving a PIP pressure-limiting vessel up and down, as described herein. The positive end expiratory pressure (PEEP) may be adjusted similarly, for example, by adjusting a PEEP pressure-limiting vessel up and down, as described herein. In some cases, the tidal volumes on inhale and exhale may be adjusted by moving an electric eye sensor up and down, as described herein. In some cases, the minimum flow detectable in the flow sensors may be adjusted by moving an electric eye up and down, as described herein. In some cases, the triggered breathing pressure may be adjusted by a moving an electric eye sensor up and down, as described herein. In some cases, all of the mechanical adjustments described above may include mechanisms that attach the part to be moved to a slider on a panel that can be adjusted by user. For example, the panel may have 7 user-adjustable sliders, one for each of the adjustments described above. In some cases, the panel also has two knobs to adjust delays relating to breathing rate.

In some embodiments, the ventilator systems described herein include one or more pressure-limiting subsystems, and/or one or more pressure-limiting and pressure-limit detection subsystems, containing a liquid (e.g., water or oil). In some cases, pressure-limiting subsystems include a vessel containing a liquid (e.g., water or oil) and a tube submerged in the water, where the depth of the tube limits the pressure in the tube above the liquid in the vessel.). In some cases, pressure-limiting and pressure-limit detection subsystems include a vessel containing a liquid (e.g., water or oil) and a tube submerged in the water, where the depth of the tube limits the pressure in the tube above the liquid in the vessel, and where a detector (e.g., an electric eye) is used to determine if the pressure limit is exceeded (e.g., by detecting bubbles in the liquid).

In some embodiments, a method for using a ventilator system described herein includes the following steps. In some cases, an operator opens a door, inserts a removable airway manifold, and fills it with water (or oil) in the correct places (e.g., in pressure-limiting subsystems). The door may be located at the back of the unit opposite a control panel, where the control panel is coupled to movable sensors. The operator may then close the door, and may attach the unit to a patient and a gas source. The ventilator may also include a means (as described above) for generating and adjusting a mixed gas with a particular $FiO_2$, such that the input gas (e.g., to an inhale line of the ventilator system) may be pure $O_2$ mixed with another gas (e.g., air, or nitrogen), and the operator may open a valve (e.g., that is part of the ventilator system, or part of a system outside of the ventilator system) to introduce the input gas into the system. In some cases, the ventilator system can be coupled to an air source (e.g., an air compressor, or a mixed gas (e.g., $FiO_2$) generating system) using a self-sealing fitting, and no valve between the air source and the ventilator is needed. The pressure-limiting subsystems (e.g., PIP and PEEP vessels, as described herein) may also be connected to the rest of the system by the operator, such as via snapping them into one or more holders that are connected to a slider for adjustment up and down on the control panel.

In some cases, the ventilator systems described herein may include a screen-type user interface (e.g., an LCD display). In some cases, the ventilator system may include an LED-based user interface (e.g., with a set of LED indicators, or a set of LEDs forming a display). In some embodiments, the interface displays the sequencing of the valves, and flow, and other sensor data (e.g., from electric eyes). Patient data may also be stored and output by the control system.

In some embodiments, the ventilator systems described herein include one or more flow sensors, one or more pressure sensors, and one or more temperature sensors. The flow, pressure, and/or temperature sensors can have portions in the removable unit (airway) and/or in the base unit. The temperature sensor may be non-contact, such as by using an infra-red detector to determine the temperature of the air inside the airway. Non-contact temperature measurements can be taken, for example, through a window, or by detecting the surface temperature of a region or regions of the airway as an indicator of the temperature inside the airway. A temperature sensor may in some cases have a contact in the base unit that comes in contact with a region or regions of the airway, where the contact in the base unit may include a temperature sensor such as a thermistor.

In some embodiments, active components of sensors (e.g., pressure and flow sensors) may be incorporated into the removable unit (or airway) of the ventilator systems described herein. For example, a heat source such as a hot wire and a temperature sensor such as a thermistor may be disposed in the airway, with external electrical connections to a mating part on the base unit, to enable what is generally known as hot-wire anemometry. Pressure sensors such as MEMS sensors may also be disposed in the airway with external electrical connections that mate to a base unit. The removable unit may contain a power source such as a battery, or have connections to a power source via a plug or contact-based connector, or have a wireless source of energy, such as by using a Qi standard. The removable unit may also include electronics (e.g., a processor to process measurements taken by one or more sensors, a communication unit to wirelessly communicate with a communication unit and a processor in the base unit, and/or wireless power receiver(s)). The sensors in the removable unit may send (or communicate) a measurement to the electronics in the removable unit, and optionally information from the measurement may be transmitted wirelessly to the base unit.

In some embodiments, the ventilator systems described herein include a flow sensor that can detect a flowing gas, or a flow rate of a gas, where the gas may contain other material (e.g., particles). The flow sensors (or detectors) described herein may be, or have portions that are, a stand-alone unit that can be connected to an inlet and an outlet tube or pipe. The flow detectors described herein may be a system that is, or have portions that are, fixedly couplable (or attachable) to a tube or pipe, such as via a clamp.

In some embodiments, ultrasonic flow sensors may be arranged to measure flow within the airway in the removable unit (or airway). In some embodiments using ultrasonic flow sensors, there are no active components in the removable unit. A mating subsystem of the removable airway may contain tubing, and optionally a means (e.g., a slot, or a pin, or other alignment structure) to fixedly couple the mating subsystem to the ultrasonic source and sensors in the base unit. The tubing may be metal, plastic, or other suitable material for transmitting ultrasound.

The ventilator systems described herein may include tubes or tubing. The tubes or tubing may include a volume contained by surfaces adjacent to the volume with at least two openings to the volume, such as an inlet and an outlet. The geometry of the tubes or tubing is not limited. For example, a tube or tubing may have an approximately cylindrical volume, a volume with an approximately square or rectangular cross-section, a volume with a semicircular cross-section, or any other geometry. In some cases, a section of a tube or tubing may be a portion of a sensor. In some cases, the tubes or tubing may have a section removed, and replaced with a portion of a sensor. For example a tube or tubing may have a hole cut out of one of the sides, or may be formed with a hole in one of the sides, of the tube or tubing and the hole covered with a compliant region (e.g., forming a portion of a pressure sensor, as described herein) or a diaphragm (e.g., forming a portion of an acoustic flow sensor, as described herein). The hole covered by the portion of the sensors may also be sealed, such that no air can escape the tube or tubing through the hole of (or adjacent to, or in the vicinity of) the sensor portion. In some cases, the tubes or tubing may have separate sections, where the separate sections may be of different materials or dimensions. For example, a portion of the tubing that is used in the pinch valve (e.g., a portion of the tubing in the vicinity of the pinch valve) may be a highly compliant material such as silicone, and the tubing upstream and downstream from the pinch valve may be vinyl, which is less compliant. This may be advantageous in that vinyl tubing may be less expensive than silicone tubing, thus lowering the overall cost of the removable unit by using silicone tubing only in the regions where high compliance is required.

In some embodiments, ventilator systems described herein may measure flow with optics, such as by interferometry or by a Schlieren-type shadowgram (e.g., using Schlieren photography, or shadowgraphs). Such systems measure flow that is related to disturbances in the airway such as turbulence or induced Karman vortices. Such sensors could include an optical system (e.g., including a light source and a detector, where the detector is an array of photodetectors, or a camera (e.g., a CCD camera)), and one or more windows for light to enter and exit an airway containing a flowing gas. Light from the sensor's optical system would pass into the airway via a first window (or first window portion) including an optically transmissive material. The light would exit the airway through a second window (or second window portion) after interacting with the gas in the airway. The first and second windows may be the same window or different windows, and the first and second window portions may be portions of the same window, or portions of different windows. The first and second windows (or window portions) may be flat such that they do not distort or redirect the incoming light, or may be one or more lenses.

In some embodiments, ventilator systems described herein may measure flow using a mechanical means in the removable airway, such as using a paddle wheel or turbine in the air flow within a tube. Air flow within the removable airway would cause the wheel or turbine to rotate. The movement of the paddle wheel or turbine can be measured by external (i.e., in the base unit) light source and detector means (e.g., an electric eye, as described herein), whereby the paddle wheel interrupts the light from the source (e.g., by impinging upon a part of a rotating wheel or turbine) and changes the intensity detected by the detector as the rotating part moves. The light may be reflected, refracted, diffracted, or pass through in such a position that it is interrupted and then not interrupted periodically. The flow sensors can be calibrated, such that the rate of the changes in light intensity can be converted to the speed of the rotating means and the flow rate. In some embodiments, the rotating wheel or turbine may have a means for slowing the rotation as by braking. The brake may be used to detect lower flows after a period of higher flow where the wheel may continue spinning due to momentum of the wheel at a speed which would indicate a higher flow than the actual reduced flow, where the brake may be temporarily applied to reduce the speed of the wheel such that the wheel's speed may sooner represent the actual flow rate. The brake may be electrostatic, wherein at least two generally adjacent conductive regions are placed outside the airway to which a potential difference is applied, in the manner of an electrostatic gripper or chuck. The brake may be turned on periodically and or at regular intervals, such as every tenth of a second, or every 1 second. This can aid in the detection of reduced flow rates, as the rate at which the wheel slows down may be less than the rate at which the flow drops resulting in a measurement with a time lag. The brake may also include an electrorheological or magnetorheological fluid contained within a system coupled to the rotating wheel or turbine within the airway and acted upon by an electric or magnetic field. The electric or magnetic field may be provided by a subsystem in the base ventilator, or by a subsystem within the airway (e.g., where electrical energy is provided by the base ventilator system via an electrical connection to the airway).

In some embodiments, the ventilator systems described herein include one or more flow sensors that can detect the transduction of sound generated by a flowing medium such as a gas. In some embodiments, the ventilator systems described herein include one or more flow sensors that detect a flow (e.g., within a tube) by measuring a sound generated by a flowing medium such as a gas. In some cases, the sensor may include a portion (e.g., that is part of the removable unit or airway) with an inlet and an outlet. In some cases, the sensor may include components that detect sound, for example, sound generated by gas flowing in a tube, where the components are outside the tube (e.g., where the components are part of a portion of the sensor contained in a base unit). In some cases, a first component of the sensor is coupled to (or inside of) the tube (e.g., that is part of the removable unit or airway) and a second component of the flow sensor is outside (and not connected to, or not touching, or touching but not connected to) the tube (e.g., that is part of the base unit).

In some embodiments, the ventilator systems described herein include one or more acoustic flow sensors that measure the flow of a fluid by measuring the sound(s) generated from the flowing fluid. In some cases, acoustic flow sensors contain a diaphragm that forms a part of (or is coupled to) a tube of the removable airway, wherein air (or are with other material) flowing in the tube cause the diaphragm to emit a sound. The acoustic flow sensors may further include a sound sensor (e.g., microphone) included in a base unit configured to measure the sound generated by the diaphragm. In some cases, the tube of the removable airway further includes one or more structures configured to generate sound, as described herein. In some cases, insulating regions surround (or are adjacent to) a portion of the tube that generates sound in response to flow within the tube and/or the microphone, to insulate the tube region and/or the microphone from sounds (e.g., noise) generated outside of the portion of the tube, as described herein. In some cases, the acoustic flow sensors contain structures and or more than one microphone to detect a rate and a direction of flow within a tube. The sound generating region(s) (e.g., diaphragms and/or structures in the tube) may be in more than one location within the tube, and/or may surround the tube. The sound generating region(s) may be a section of the tube such as a thin section (diaphragm) such that sound is emitted generally radially outwards all around the tube. In some cases, a chamber may be disposed around the tube to collect sound from many directions emitted by the tube. In some cases, the tube sections adjacent to the sound sensing section may contain sound blocking elements to isolate a sound sensor (e.g., microphone) from environmental sound, such as by forming a path that snakes back and forth, and may contain sound-absorbing and dampening surfaces.

In some cases, a first portion of a flow sensor is a tube that is part of the removable unit (airway), and a second portion of a flow sensor is a microphone that is part of the base unit. In such cases, the tube may be configured to transmit sound in a frequency range of interest (e.g., in a frequency range where a flowing gas in the tube will generate sound, and where the microphone can detect the sound). For example, the material of the tube may be chosen to transmit sound, and/or the tube may be designed to efficiently generate sound in response to a flowing gas within the tube (e.g., contain structures as described herein).

In some embodiments, the flow rate may be detected by placing an accelerometer (that is part of the base unit) against the diaphragm (that is part of the removable unit) of an acoustic flow sensor. In such cases, the support and connection of the accelerometer to the base unit would favorably have a lower compliance than the diaphragm. In some embodiments, the movement of the diaphragm may be detected by having light from the base unit impinge on the diaphragm and subsequently be detected by a light detector in the base unit, wherein changes in the light due to movement of the diaphragm may be detected. In some cases, an accelerometer, for example forming a portion of an acoustic flow sensor, may be incorporated into the removable unit.

In some embodiments, a diaphragm may contain a coil of wire, and the base unit may contain a magnetic-field generating means, such as a permanent magnet. The coil of wire on the diaphragm may have electrical connections, for example at positions that are fixed on a rigid section of the removable unit. The electrical connections may couple to electronics (e.g., the control system) in the base unit for detecting a current in the coil. When the coil moves due to sound generated from the flowing gas within the airway, it will generate a current due to a proximity of the coil to the magnetic field provided by base unit. The coil may be similar to coils used in common speakers. In an alternate embodiment, a magnetic field generating means, such as a magnet, may be mounted on the diaphragm, and a magnetic field detecting means, such as a coil or a magnetometer, may be in the base unit. In some embodiments, the magnetic field generating means on the diaphragm may be a coil. In some cases, the field generating means and the field sensing means (e.g., a coil, magnetometer, Hall sensor, or any device capable of detecting a magnetic field) may be coupled via a negative feedback amplifier system (e.g., in the control system) such that the amplifier drives field sensing or field generating means coupled to the diaphragm (e.g., a coil) in such a manner that the field sensing or field generating means coupled to the diaphragm remains in a steady state, such as an approximately fixed position, or vibrating at an approximately fixed amplitude or frequency. The signal in the negative feedback amplifier that results in the approximately steady position of the diaphragm may be used as a signal representing the amplitude of sound within the airway.

In some cases, an acoustic flow sensor may also measure other parameters of a flowing gas, such as pressure and/or temperature. In some cases, an acoustic flow sensor may work in conjunction with another one or more sensors that measure other parameters of a flowing gas, such as pressure and/or temperature. A processor (e.g., that is part of the control system) may convert the detected sound (e.g., intensity and/or frequency) and another detected parameter (e.g., temperature and/or pressure) to a flow rate of the gas. In some cases, a measured flow rate of a gas and another detected parameter (e.g., temperature and/or pressure) can be used by the control system to convert a gas flow rate to an amount of gas (e.g., air, or oxygen) moving past (or through) the sensor (or moving within a tube). In some cases, the total amount of gas moving through the sensor system may be calculated from inputs from independent flow, pressure, and temperature sensors.

In some cases, the gas within the ventilator system is air, where the air may be any suitable gas used in the ventilator systems described herein, such as a combination of oxygen and air in various proportions, air exhaled from a patient that also contains other material (such as liquid particles, pathogens, and/or medicinal aerosols), or air mixed with any other contaminants (e.g., from the patient, or a gas source coupled to the system).

In some cases, the flow detectors (sensors) described herein may have a means to calibrate the detected sound to a flow rate, for example, where such flow rate is measured by a preconfigured and calibrated detector system. The flow sensors described herein may have adjustments or inputs of calibration data or settings. The airway may have calibration data stored in a machine-readable format printed on its surface, such as linear or 2D barcode.

In some embodiments, the ventilator system described herein contain pressure sensors that have components in removable unit (airway) and in the base unit. In some cases, pressure may be measured by deformation of a surface (e.g., a compliant region) of the removable airway. The deformation may occur in a region that has a lower compliance than the surrounding region enclosing the airway such that when the pressure in the airway increases, the softer region pushes outwards. The deformation of the compliant region may be detected using one or more sensor portions (e.g., force sensors, load cells, or electric eyes) contained in the base unit, as described herein. In some embodiments, the pressure sensor may include a driven oscillator and changes to the oscillation may be converted into a pressure. Such a system may be composed of a coil mounted on a diaphragm and a permanent magnet mounted on the base, where the coil is driven at a fixed amplitude and frequency. Changes in amplitude, phase, or frequency may be translated into pressure changes.

In some cases, the airway may also contain a humidity sensor.

In some cases, a calibrating system may be attached to the inspiratory and expiratory ports of the removable airway while it is in place in the base ventilator unit of the ventilator. The calibrating system may have active sensors, such as flow, pressure, and temperature sensors, and may contain an electrical port to connect to the base ventilator system. The base unit may have a setting or be configurable to flow gas at a set rate or at a range of rates that may be detected by the calibrating system. In this manner, the calibration of the airway may be checked and adjusted either with manual inputs or automatically via an electrical connection from the base unit to the calibrating system. The calibrating system may also include a fixed tube, such that at a predetermined setting of the valves a known amount of gas is expected to flow in the fixed tube, and a measured flow may be compared to the expected flow to calibrate the ventilator system. A fixed tube may be a tube that has a rigid and fixed geometry, for example a tube that is molded in rigid plastic and is provided as a component of the ventilator system. The ventilator base unit may have preprogrammed settings and/or sequences of settings and readings considered as a calibration routine that may be built into the ventilator system (e.g., into the control system).

EXAMPLE SYSTEMS

FIG. 1 is a simplified schematic of an example of an inhale manifold 1000 of a ventilator system, in accordance with some embodiments. The inhale manifold 1000 contains tubes 1, 4, 6, 10, 14 and 27, connectors 3 and 13, bellows 7, weight 8, valves 5 and 9, pressure-limiting and pressure-detection subsystem 11, flow sensor subsystem 12, and pressure sensor subsystem 31. Tube 1 contains gas to deliver to the patient (e.g., a mixed gas with a particular $FiO_2$, pure air, or pure oxygen). Inhale manifold 1000 may contain a device or subsystem (not shown) for the generation of a mixed gas with a particular $FiO_2$ from pure oxygen. The tube 1 connects to a connector 3 to a tube 4, with a direction of gas flow 2. Tube 4 connects to valve 5, which connects to tubes 6. Tubes 6 connects to bellows 7, and valve 9. The outlet of valve 9 connects via tube 10 to a pressure-limiting and pressure-detection subsystem 11 and flow sensor subsystem 12. The outlet of flow sensor subsystem 12 connects via tube 27 to a connector 13 which connects to tube 14 which leads to the patient inhale tube, such as the inlet of patient circuit, where gas flows in direction 15.

Figure 2:
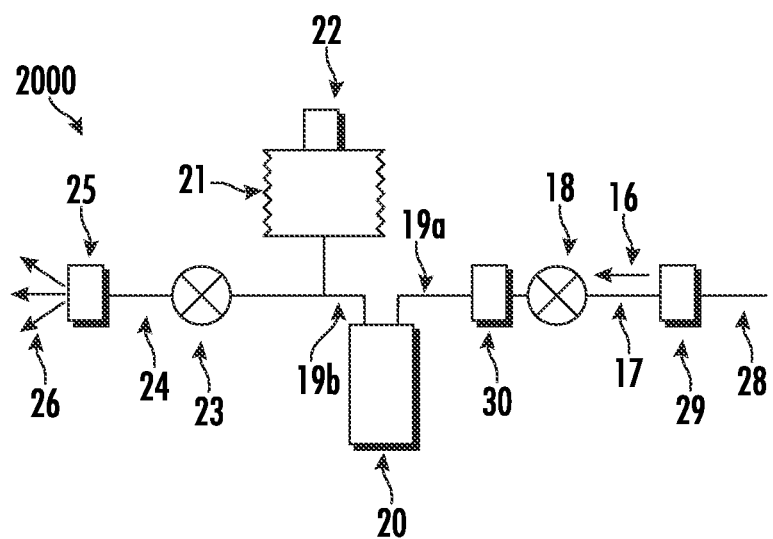
FIG. 2 is a simplified schematic of an example of an exhale manifold of a ventilator system, in accordance with some embodiments.

FIG. 2 is a simplified schematic of an example of an exhale manifold 2000 of a ventilator system, in accordance with some embodiments. The exhale manifold 2000 contains tubes 17, 19a, 19b, and 24, connector 29, bellows 21, weight 22, valves 18 and 23, pressure-maintaining subsystem 20, flow sensor subsystem 30, and exit port (e.g., including a filter) 25. Tube 28 leads from a patient's lungs such as via a patient circuit and/an endotracheal tube to a connector 29 which connects to tube 17, with gas flow direction 16. The inlet tube 17 connects to valve 18. The outlet of valve 18 connects to the tube 19a. Tube 19a connects to the pressure-maintaining subsystem 20. Gas passing through the pressure-maintaining subsystem 20 enters tube 19b and a bellows 21. Tube 19b connects also to valve 23, whose outlet tube 24 connects to exit port 25 which expels gas 26 to atmosphere. The output of valve 18 may also pass through a flow sensor 30.

There are several modes of operation of a ventilator system including inhale manifold 1000 and exhale manifold 2000. A control system (not shown) may monitor signals from pressure-limiting and pressure-detection subsystem 11, flow sensor subsystem 12, pressure sensor subsystem 31, pressure-maintaining subsystem 20, and flow sensor subsystem 30, and then adjust (e.g., based on the signals) valves 5, 9, 17 and 23, and other components of the system (e.g., bellows 7 and/or 21). The control system adjusts the valves in the ventilator system according to different modes of operation.

In a tidal volume inhalation control mode, valve 5 is opened and valve 9 is closed. The bellows 7 which will be described below inflates (e.g., due to air pressure) to a pre-determined volume, such as 500 cc, from 50 cc to 1000 cc, or from less than 50 cc to more than 1000 cc. When the predetermined volume has been reached, the control system closes valve 5 and opens valve 9. Valves 18 and 23 may be open or closed during inflation of the bellows 7. When valve 9 opens (e.g., and valve 18 and/or 23 is closed), gas begins to inflate the lung of the patient (not shown), and pressure builds in the pressure-limiting and pressure-detection subsystem 11. For example, valve 18 may be closed when valve 9 opens such that bellows 22 is isolated from the patient while gas from the inhale manifold 1000 inflates the lung of a patient. In cases where there is no bellows 22 on the exhale manifold 2000, then valve 23 may be closed and valve 18 may be open, or both valves 18 and 22 may be closed. When pressure in pressure-limiting and pressure-detection subsystem 11 reaches a predetermined value, or PIP (e.g., about 30 $cmH_2O$, about 40 $cmH_2O$, or from 15 $cmH_2O$ to 45 $cmH_2O$, or from less than 15 $cmH_2O$ to more than 45 $cmH_2O$), valve 9 is closed by the control system, completing the inhale cycle. Valve 5 may then be opened to fill the bellows 7 to be ready for the next inhale cycle of this mode.

When valve 9 closes, the exhale cycle of this mode may commence. The control system may have a predetermined user-settable or fixed delay, such as 1 second or less to 3 seconds or more, such that valve 18 may open after the delay has passed. The delay may be zero in some cases. When valve 18 opens, gas begins to pass from the lungs into the tube 19a. In one mode, valve 23 may be closed during a first portion of the exhale cycle. Subsystem 20 maintains the pressure at or above a preset value (e.g., about 5 $cmH_2O$, or from 2 $cmH_2O$ to 15 $cmH_2O$, or from less than 2 $cmH_2O$ to more than 15 $cmH_2O$), and the bellows 21 fills with exhaled gas. Gas may also flow through a flow sensor subsystem 30. The end of the first portion of the exhale cycle may be determined either by the bellows 21 reaching a predetermined volume, or by the flow sensor 30 detecting a predetermined low level of flow, such as no flow, or by the pressure sensor reaching a preset minimum value (PEEP). When any of these end-of-exhale conditions is reached, the control system closes valve 18 and open valve 23, initiating a second portion of the exhale cycle. In the second portion of the exhale cycle, gas in the bellows 21 is emitted through filter 25 to the atmosphere, thereby completing the exhale cycle. After the exhale cycle is complete, there may include a delay (e.g., of 1 second or less and up to 3 seconds or more) before repeating the inhale cycle, as described above.

In another mode of operation, a pressure control mode, the ventilator system uses the PIP, as determined by a preset value of the peek pressure-limiting and pressure-detection subsystem 11, to control the system. In this mode, both valves 5 and 9 are opened simultaneously (e.g., and valves 18 and/or 23 are closed) at the start of an inhale cycle. The lungs of the patient inflate to a pressure that stops increasing due to the action of the pressure-limiting and pressure-detection subsystem 11. When the limiting pressure is reached, the control system receives a signal from pressure-limiting and pressure-detection subsystem 11 (e.g., indicating that a PIP has reached a threshold value, e.g., about 30 $cmH_2O$, about 40 $cmH_2O$, or from 15 $cmH_2O$ to 45 $cmH_2O$, or from less than 15 $cmH_2O$ to more than 45 $cmH_2O$), and the control system closes valve 9. The exhale cycle is then initiated as described above with respect to the tidal volume inhalation control mode (e.g., with suitable delays). As above, the end of the exhale cycle may be determined via flow sensor 30 or a volume of bellows 21. After the exhale cycle is complete, there may include a delay (e.g., of 1 second or less and up to 3 seconds or more) before repeating the inhale cycle described above.

The preceding two modes of operation are commonly referred to as "Mandatory Breathing" mode. Another clinically desirable mode is commonly referred to as "Triggered" or "Spontaneous" breathing mode. In a triggered breathing mode, at the end of an exhale cycle, with valve 9 closed and valve 5 open, pressure sensor subsystem 31 may be monitored for a negative pressure (e.g., about negative 2 $cmH_2O$, or from negative 4 $cmH_2O$ to negative 2 $cmH_2O$, or from less than negative 4 $cmH_2O$ to more than negative 2 $cmH_2O$), and a negative pressure threshold may be set to a predetermined value. When the negative pressure threshold in pressure sensor subsystem 31 is reached or the pressure is pressure sensor subsystem 31 more negative than the threshold, then the control system may open valve 9. The pressure-limiting and pressure-detection subsystem 11 may be set to a predetermined value (e.g., about 10 $cmH_2O$, or from 4 $cmH_2O$ to 20 $cmH_2O$, or from less than 4 $cmH_2O$ to more than 20 $cmH_2O$), such that the breathing is assisted by a background pressure above atmospheric pressure. The end of the inhale cycle in this triggered breathing mode may be determined by the flow sensor subsystem 12 detecting a preset low level of flow (e.g., about 3 liters per minute (lpm), from 0.1 lpm to 10 lpm, or from 1 lpm to 10 lpm, or from 0.1 to 1 lpm). In this mode, the exhale cycle may be the same as described above for the mandatory breathing modes, and the exhale cycle end may be determined by volume exhaled or by flow rate. Additionally, after the exhale cycle is complete, there may include a delay (e.g., of 1 second or less and up to 3 seconds or more) before repeating the inhale cycle for the triggered breathing mode (as described above).

The valves 5, 9, 18 and/or 23, in inhale manifold 1000 and exhale manifold 2000 may be pinch valves, in some embodiments. Valves 5, 9, 17 and/or 23 may be configured to variably adjust the flow of gas through the valve (i.e., through a tube passing through the valve, or through a compressible section of a tube passing through the valve), as described herein.

Figure 3A:
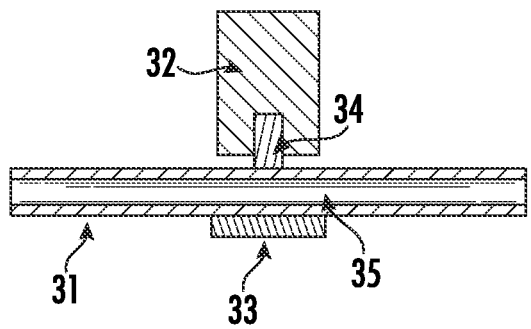
FIGS. 3A and 3B are simplified schematics of an example of a pinch valve, in accordance with some embodiments.
Figure 3B:
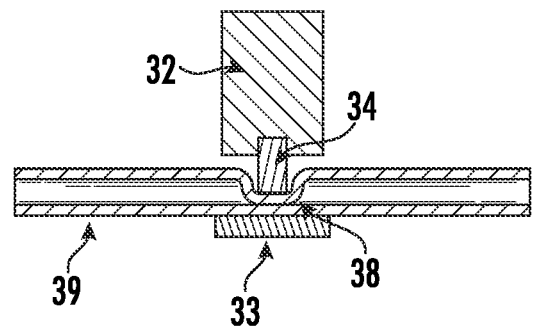

FIGS. 3A and 3B are simplified schematics of an example of a pinch valve, in accordance with some embodiments. FIG. 3A shows the valve in an open state (or position), and FIG. 3B shows the valve in a closed state (or position). The valve in this example contains valve body 32, a moveable element 34, and a fixed element 33. In FIG. 3A gas-containing tube 31 passes through the open valve where tube region 35 is in an open state. When an actuator (not shown) within the valve body 32 is actuated, element 34 is pushed into tube 39, closing the valve. FIG. 3B shows the valve in a closed state, where the moveable element 34 compresses the tube 39 against fixed element 33 in a tube region 38. Tube region 38 is a compressible section of the tube 39. In some cases, when the valve is closed the tube is closed and no gas (or a limited amount of gas) can pass at pressures reached in the ventilator system. The valve body 32 is fixed spatially with respect to the tube backstop 33. When the valve in this example is open, such as when the moveable element 34 is in the position shown in FIG. 3A, the tube 31 can be removed from the valve. The valve shown in FIGS. 3A and 3B may be configured to variably adjust the flow of gas through the valve (i.e., through a tube passing through the valve, or through a compressible section of a tube passing through the valve), as described herein. For example, moveable element 34 may have a plurality of positions configured to compress the tube 31 by varying amounts.

Figure 4A:
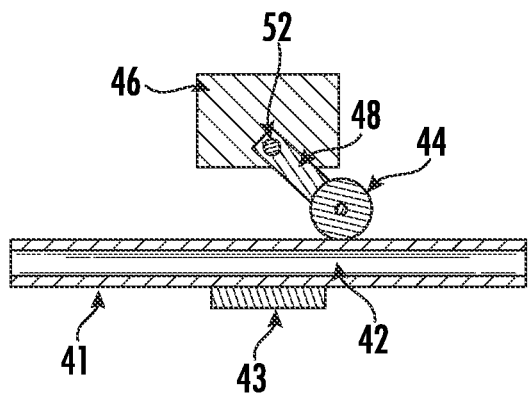
FIGS. 4A and 4B are simplified schematics of another example of a pinch valve, in accordance with some embodiments.
Figure 4B:
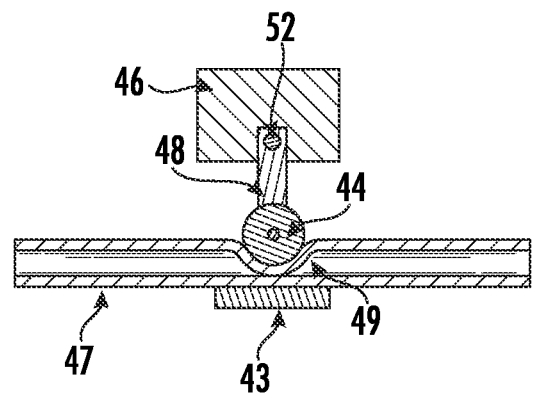

FIGS. 4A and 4B are simplified schematics of another example of a pinch valve, in accordance with some embodiments. FIG. 4A shows the valve in an open state (or position), and FIG. 4B shows the valve in a closed state (or position). The valve in this example contains valve body 46, a roller 44, an arm 48, an axle 52, and a fixed element 43. In this example, a roller 44 may compress the tube 41 by rotating around axle 52 on arm 45. The rotation of arm 45 is actuated via a rotary actuator in valve body 46. FIG. 4A shows the arm 48 and the roller 44 at open positions and tube region 42 of tube 41 is open, such that gas may pass through region 42. FIG. 4B shows the arm 48 and the roller 44 in a closed position, where the roller 44 is pushed into tube 47 and tube region 49 is compressed against fixed element 43 such that no gas (or a limited amount of gas) can pass at pressures reached in the ventilator system. Tube region 49 is a compressible section of the tube 47. The valve body 46 is fixed spatially with respect to the tube backstop 43. When the valve in this example is open, such as when the arm 48 and roller 44 are in the positions shown in FIG. 4A, the tube 41 can be removed from the valve. The valve shown in FIGS. 4A and 4B may be configured to variably adjust the flow of gas through the valve (i.e., through a tube passing through the valve), as described herein. For example, arm 48 may have a plurality of positions configured to compress the tube 41 by varying amounts.

In some cases, the rotary actuator is a motor, such as a gearhead motor. An advantage of the valve shown in FIGS. 4A and 4B is that a wide range of motor specifications will meet the need of the valve. In some cases, a rotation rate of the output shaft in RPM has a minimum value of 30 RPM or less, and a torque minimally sufficient to be able to compress the tube.

Figure 5:
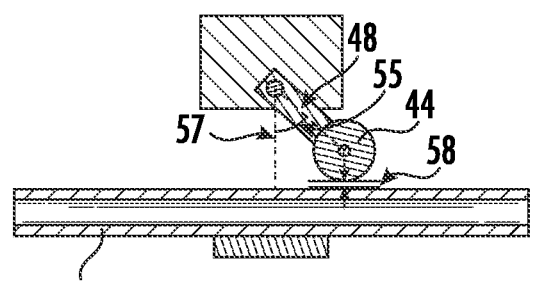
FIG. 5 is a simplified schematic of the pinch valve shown in FIGS. 4A and 4B, in accordance with some embodiments.

FIG. 5 is a simplified schematic of the pinch valve shown in FIGS. 4A and 4B, in accordance with some embodiments. The time to close the valve in this example may be minimized by having an open position where the roller 44 is close to the tube 41, with a small distance 58 between the roller 44 and the tube 41, as shown in FIG. 5. In this example, the angle 55 between the arm 48 and a line 57 (where line 57 is approximately perpendicular to the tube) is a fraction of 360 degrees, such as 30 degrees, and the distance in the open position between the roller and the tube is small, such as 0 mm or 1 mm, or 2 mm, or from 0 mm to 3 mm, or from less than 1 mm to more than 3 mm. If the rotation rate of the arm 48 is 30 RPM, and the angle 55 is 30 degrees, then the time to close the valve is approximately 0.3 seconds. A lower RPM may also be used if a longer closing time is acceptable. A higher RPM may be used if a shorter closing time is required. In some cases, the open position of the valve shown in FIG. 5 allows insertion and removal of the tube. In some cases, the valve has an open position used during operation, and a tube removal position where the roller 44 is moved away from tube 41 when the tube 41 is removed from the valve.

In some cases, pinch valves with rotary elements for the ventilator systems described herein can use motors with 30 RPM and a torque of 40 gram-cm. For example, such a motor can be used to compress a silicone tube (e.g., with a ½" diameter).

The tubes in the ventilator systems described herein, e.g., those shown in FIGS. 1-5, may be of any flexible material such as vinyl or silicone. The motor used by the valves in the ventilator systems described herein, e.g., those shown in FIGS. 1-5, may be a DC motor. A control circuit may position the motor by turning it on and off. In some cases, the position of the motor may be determined by an electric eye, where the electric eye includes a light emitter and a light sensor.

Figure 6A:
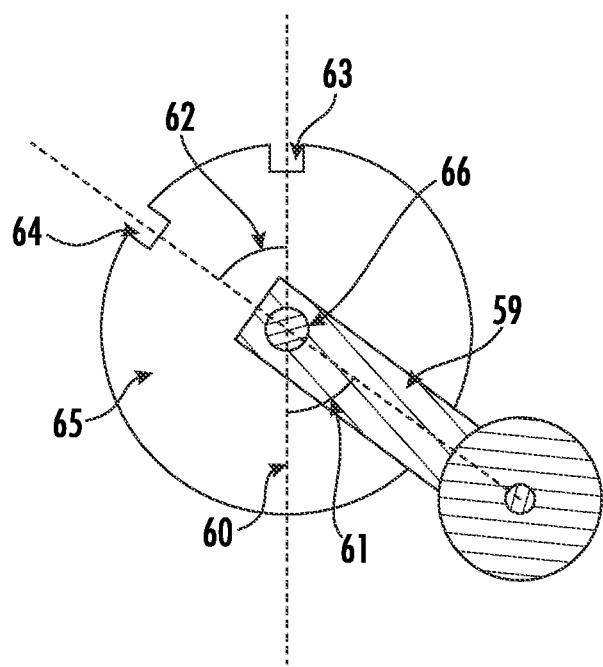
FIGS. 6A and 6B are simplified schematics, in front view and side view, respectively, of an example of a system for controlling the position of a valve, in accordance with some embodiments.
Figure 6B:
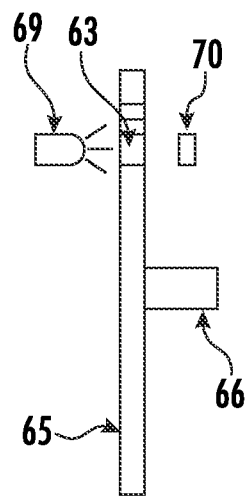

FIGS. 6A and 6B are simplified schematics, in front view and side view, respectively, of an example of a system for controlling the position of a valve, in accordance with some embodiments. The system shown in FIG. 6A includes a generally non-light-transmissive (or opaque) disc 65 mounted on a rotary actuator shaft 66. The arm 59 may be the same as arm 48 in FIGS. 4A, 4B and 5. The disk 65 has two slots 63 and 64 cut into it, and an angular separation 62 generally the same as the angle 61 between the arm 59 and a direction 60 similar to direction 57 in FIG. 5 (i.e., that is approximately perpendicular to the tube (not shown)). The two slots 63 and 64 may be positioned anywhere on the disc 65 as long as the angle between them is generally angle 62. A single electric eye may be disposed fixedly with respect to the disc 65 to detect two positions. FIG. 6B shows the disc 65 from a side view. Slot 63 is shown disposed between a light source 69 and a light detector 70 comprising the electric eye. When at the position shown in FIG. 6B, the detector will detect light. At other positions, it will detect less light. This difference can be used to determine by the control system when the valve is in different positions. The slots 63 and 64 can be located to correspond to certain positions of the valve, e.g., an open position and a closed position. In some cases, there can be more or fewer than two slots to indicate more than two valve positions, e.g., an open position, a closed position, and a position for removing the tube from the valve. Valves using the systems shown in FIGS. 6A and 6B may be configured to variably adjust the flow of gas through the valve (i.e., through a tube passing through the valve, or through a compressible section of a tube passing through the valve), as described herein. For example, there may be a plurality of slots (not shown) that correspond to a plurality of positions configured to compress a tube passing through the valve by varying amounts.

In operation, the rotary actuator may be turned on until light is detected through slot 63 at which point the actuator may be turned off. For example, when light is detected through slot 63, the valve is in the open position. When the valve is to be closed, the control system may turn on the rotary actuator, until light is detected through slot 64 and then the control system may turn off the actuator, leaving the valve in the closed position. The angle 62 between the slots may be more or less than the angle 61 where the control system may have predetermined delays between detecting the slot and turning off the rotary actuator. Such delays may be useful in achieving a precise closed or open position if the rotation takes some time to stop after being initiated. In some cases, the slots (e.g., 63 and 64) may be at positions in advance of the final desired resting position. The closed positions may also be controlled such that the valve does not press on the tube with too much force (e.g., which could damage the tube, or reduce the lifetime of the tube). In the case of a pinch valve with a rotating movable element, the maximum compression of the tube may be set by the geometry of the movable element (and a roller coupled thereto), or by setting limits on the position of the movable element. In the case of a pinch valve with a linear movable element, the maximum compression of the tube may be set by setting limits on the position of the movable element.

In another embodiment (not shown), instead of slots, the disc may have a contrasting region, such as darker regions, with the emitter and detector on the same side of the disc configured to illuminate and detect the contrasting regions.

Figure 7:
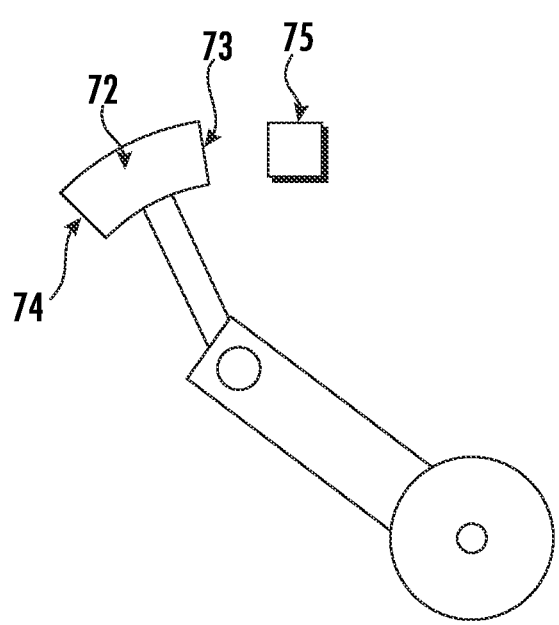
FIG. 7 is a simplified schematic of an example of a system for controlling the position of a valve, in accordance with some embodiments.

FIG. 7 is a simplified schematic of an example of a system for controlling the position of a valve, in accordance with some embodiments. In this example, the disc of the system in FIGS. 6A and 6B may be replaced with element 72 (in the example shown in FIG. 7, element 72 is a section of an annulus) with a leading edge 73 and a trailing edge 74 such that an electric eye 75 may detect a light transmission change when the edges 73 and 74 pass through the electric eye. Electric eye 75 may include a light source and detector (not shown) configured similar to that shown in FIG. 6B, or configured on the same side as element 72 as described above. Element 72 may be of any shape that has a leading and a trailing edge and is of a material that is generally non-light-transmissive for light at the wavelength of the emitter in the electric eye.

In some embodiments, a disc or other element having a generally light-transmissive material at the wavelength of the light detected by the electric eye can be used in the valve control systems described herein. In such cases, regions that are non-light-transmissive are disposed on the perimeter of the disc or other element in a manner similar to slots 63 and 64, which are detectable as a change (reduced light detection) by the electric eye they pass through it.

In other cases, a different means of detecting two positions (or a plurality of positions) of the rotation of a valve (e.g., the valves shown in FIGS. 1-5) are envisioned, such as limit switches, proximity sensors, rotary encoders, and the like. The rotary actuator of a valve (e.g., the valves shown in FIGS. 1-5) may be a DC motor, a stepper motor, a servo motor, or a pneumatic motor.

Figure 8:
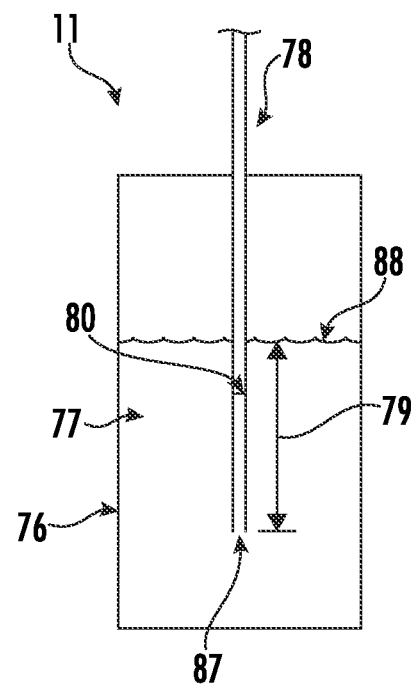
FIG. 8 is a simplified schematic showing an example of pressure-limiting and pressure-limit detection subsystem, in accordance with some embodiments.

FIG. 8 is a simplified schematic showing an example of pressure-limiting and pressure-detection subsystem 11 (of FIG. 1), in accordance with some embodiments. The pressure-limiting and pressure-detection subsystem 11 includes a container 76 that can hold a fluid 77 such as water or oil, and a tube 78. Tube 78 (e.g., a rigid tube, or a tube configured such that the height 79 is controlled) is disposed such that its distal end 87 is below the surface 88 of the liquid. In operation, if a pressure inside the tube 78 is below a pressure determined by the height 79 of a column of liquid, no gas will be released, and the surface 80 of the liquid inside the tube will be at a position between the surface 88 of the liquid and the tip 87 of the tube. When the pressure inside the tube is at or greater than that of the column of liquid of height 79, gas will escape into the liquid. Pressure above the height of the column of liquid will be released as increased flow and the pressure inside the tube will generally not exceed that of the height 79 of the column of liquid. For example, in some embodiments, the height 79 is 30 cm and the liquid is water, so the limiting pressure inside of tube 78 (and hence in a portion of the airway of the ventilator system) is 30 $cmH_2O$. This limiting pressure is commonly referred to as PIP (Peak Inspiratory Pressure). The limiting pressure may be adjusted by moving the tip of the tube 87 closer to or farther from the surface 88 of the liquid.

In some cases, pressure-maintaining subsystem 20 (of FIG. 2) in the exhale manifold may be of the same or similar configuration as described above for pressure-limiting and pressure-detection subsystem 11. In operation, when the inhale is switched over to the exhale cycle, gas in the lungs of the patient may be at a higher pressure than a desired minimum maintained pressure, such that gas nearly immediately begins to bubble out of the water. As the system is closed to atmosphere or incoming gas, it is sealed with the lungs of the patient, so gas may be released through the subsystem 20 until the minimum preset maintain pressure is reached. This pressure is commonly referred to as PEEP. The liquid container for the PEEP control is sealed, such that all gas that bubbles through enters tube 19b in FIG. 2.

Figure 9:
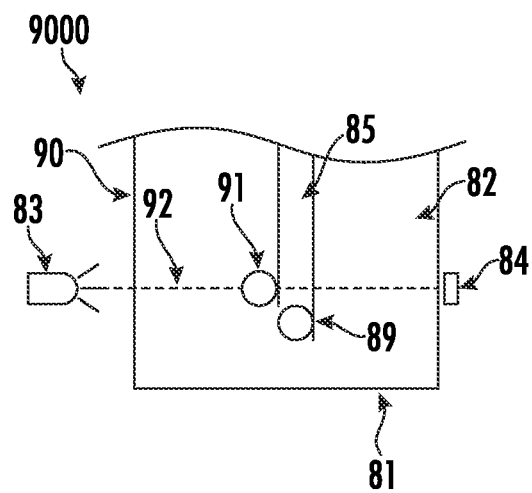
FIG. 9 is a simplified schematic showing an example of a pressure limit detection subsystem, in accordance with some embodiments.

FIG. 9 is a simplified schematic showing an example of a pressure limit detection subsystem 9000, in accordance with some embodiments. The end of the inhale cycle, or the reaching of the pressure limit, may be detected using subsystem 9000. In some cases, subsystem 9000 may be used as pressure-limiting and pressure-detection subsystem 11 in FIG. 1, and/or pressure-maintaining subsystem 20 in FIG. 2. When the pressure in the tube 85 meets or exceeds the limiting pressure set by the depth of the tip 89 of the tube below the liquid surface, bubbles will come out of the tube. The tip 89 may be cut at an angle to force the bubbles to go in a particular direction. The tip of the tube may also be bent towards a direction of desired bubble travel. Disposed outside of the liquid-containing vessel 90 is an electric eye composed of a light source 83 and a detector 84. When bubbles 91 are emitted from the tube 85, they rise and intercept the light path 92 in the electric eye, such that the electric eye detects less light when a bubble passes. In this way, a control system (e.g., controlling valves, and other components of the ventilator systems described herein) can detect the reaching of the pressure limit.

In other embodiments, the electric eye in subsystem 9000 may be configured with the emitter and detector both facing generally the same way in proximity to each other where the light from the emitter reflects off of a reflective surface, such as a retroreflective surface, or a high contrast light and dark surface. When bubbles intercept the path of the light (before and/or after reflecting off of the reflective surface) the electric eye will detects less light, and can provide a signal to control system as described above.

Figure 10:
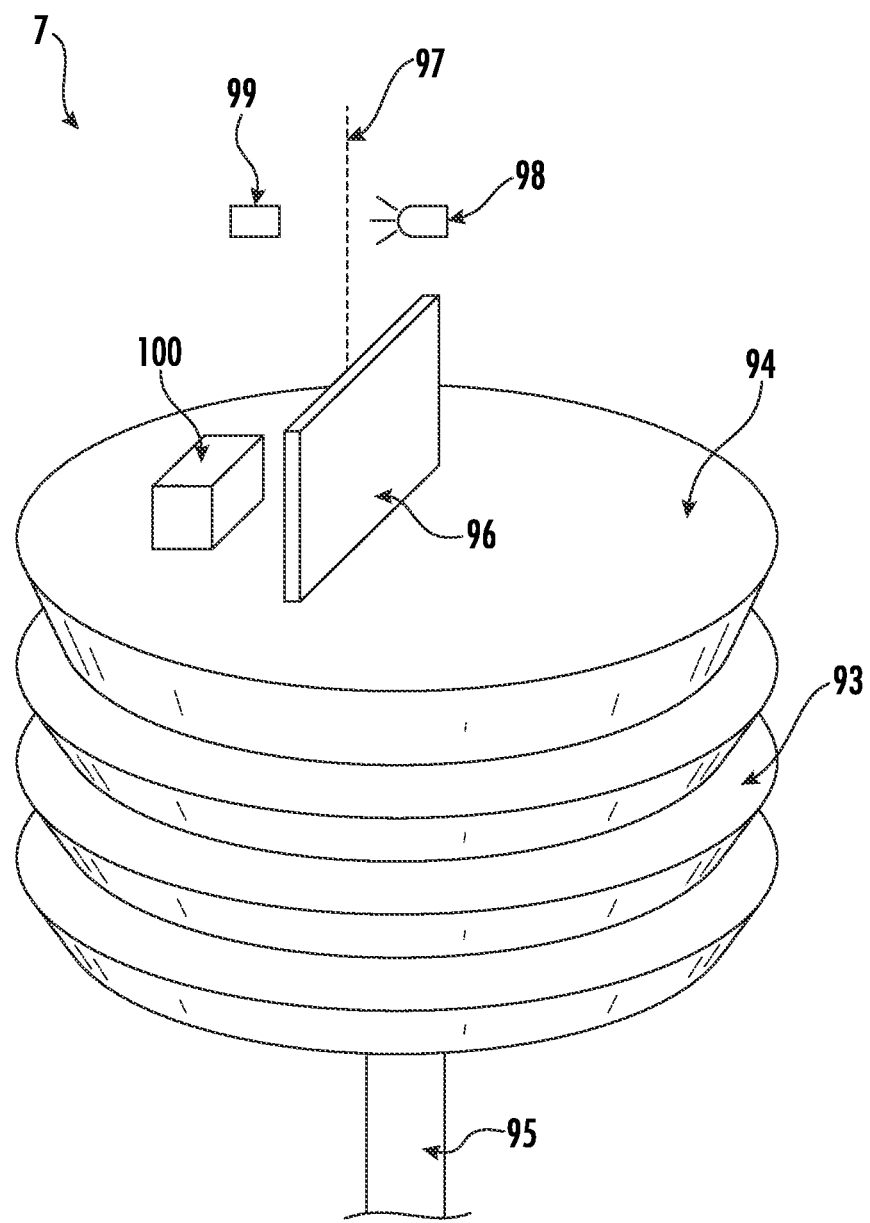
FIGS. 10-12 are simplified schematics of examples of bellows, in accordance with some embodiments.

FIG. 10 is a simplified schematic of an example of a bellows 7 (of FIG. 1), in accordance with some embodiments. The inhale cycle may be controlled by a subsystem that can have a preset fill volume, determined by bellows 7. An expandable container 93 is connected to a tube 95. When gas enters through tube 95, the container expands, with upper solid surface 94 moving in a direction 97. The upper surface has disposed on it an opaque member 96 that can rise until it interrupts the electric eye with source 98 and detector 99. The position of the electric eye determines the volume reached when the electric eye is triggered. In some cases, when the predetermined volume is reached, valve 9 is opened (e.g., by a control system that has received a signal from the electric eye that a fill volume has been reached) and the gas is transferred from the ventilator system to the lungs of the patient. A weight 100 can be disposed to compress the expandable container 93 and eject air into the lungs. In some cases, bellows 21 of FIG. 2 in the exhale manifold may be of the same or similar configuration as described above for bellows 7 of FIG. 10.

Figure 11:
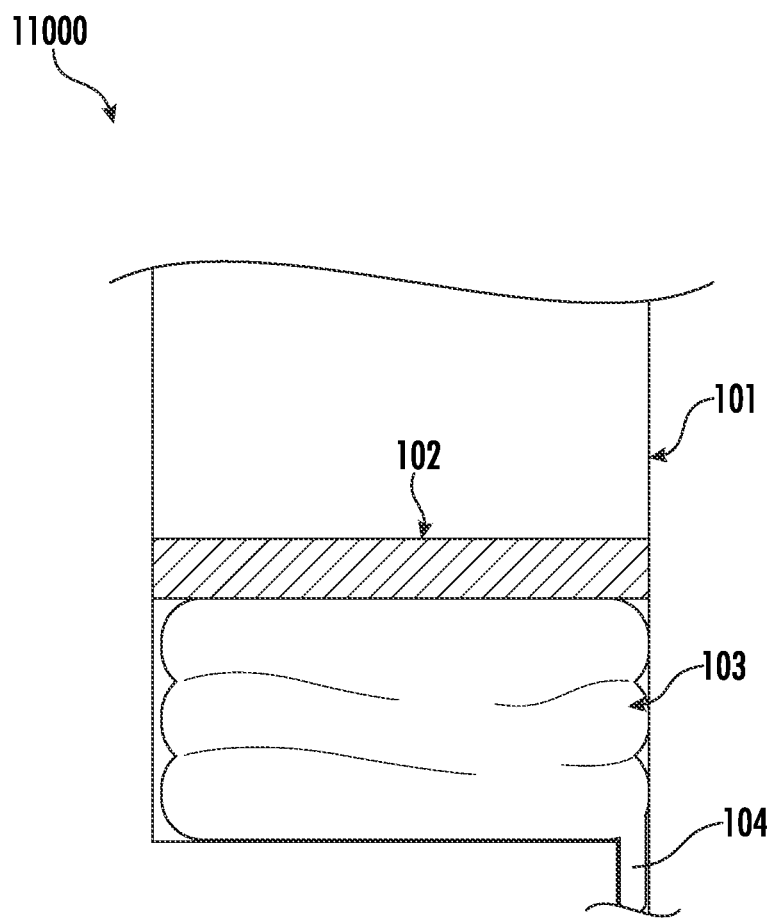

FIG. 11 is a simplified schematic of another example of bellows 7 (of FIG. 1), in accordance with some embodiments. In some embodiments, the expandable gas container of the bellows 7 is a bag of non-rigid (or flexible) material 103, such would be achieved by a silicone membrane of thickness less than 0.5 mm, as shown in FIG. 11. In this example, gas enters through an inlet 104 to a bag of non-rigid (or flexible) material 103, which when filled lifts a piston 102 held in position via a cylinder 101. The volume of gas inside bag of non-rigid (or flexible) material 103 increases as it is filled such that the piston moves up in direct proportion to the gas volume increase in the bag. In some cases, bellows 21 of FIG. 2 in the exhale manifold may be of the same or similar configuration as described above for bellows 7 of FIG. 11.

Figure 12:
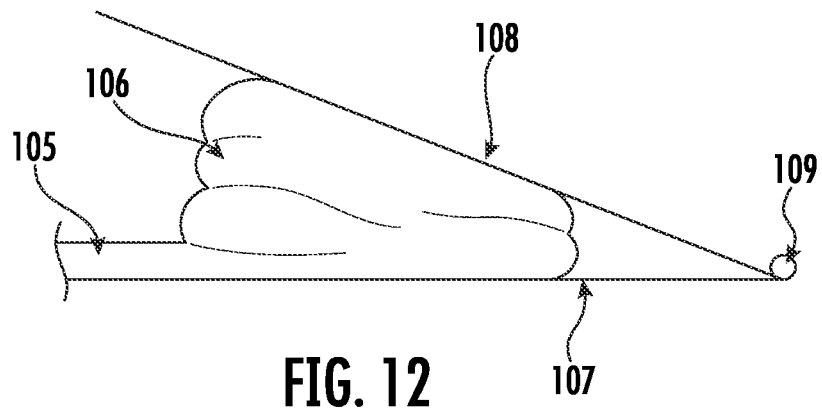

FIG. 12 is a simplified schematic of another example of bellows 7 (of FIG. 1), in accordance with some embodiments. In this example, gas enters via a nozzle 105, inflating soft bag 106, which lifts a plate 108 hinged at 109 with respect to a fixed plane 107. In some cases, the position of plate 108 is calibrated with respect to the volume of gas inside of bag 106.

In some embodiments, bellows 7 in FIGS. 1 and/or 21 in FIG. 2, each contain a generally inflatable container that expands to push an opaque means (e.g., a plate, a block, or an opaque, or reflective object) to interrupt an electric eye. The opaque means may or may not be directly connected to the inflatable container. In some cases, the opaque means may be attached to a repeatably movable means (e.g., a moving rod, wheel, or piston) that is part of the base unit.

FIGS. 13A-13C are simplified schematics of an example of pressure detection system 31 (in FIG. 1), in accordance with some embodiments. Pressure detection system 31 in this example includes a liquid 111 in a u-shaped tube 110 disposed such that direction 123 is up away from the earth, as is common in u-tube manometers. A pressure is measured directly proportional to the difference in height of the two liquid surfaces 111 and 113, where in FIG. 13A they are at the same height so there is no pressure difference on either side of the liquid 111 in tube 110. In FIG. 13B, the pressure is greater on side 125 of the tube and level 116 is below level 117. The pressure difference may be read on scale 122. In FIG. 13C, the pressure difference is negative, with height 119 detected at a preset level by the position of an electric eye including emitter 120 and detector 121. Such a negative pressure detection may be used to initiate triggered breathing. Additionally, in some cases the peak plateau pressure in the lungs (i.e., the pressure reached after inspiration is halted and pressure in the lungs equilibrates) may be measured with the manometer using the scale 122.

FIG. 14 is a simplified schematic of an example of flow sensor subsystem 12 and 30 in FIGS. 1 and 2, in accordance with some embodiments. The flow sensor in FIG. 14 includes inlet 127 into a container 128 that is generally tapered outwards from inlet 127 towards outlet 132, where up away from the earth is direction 133. A ball 129 is free to move inside the container 128. When gas enters, the ball moves upwards, out of the path of an electric eye of emitter 130 and detector 131, thus enabling the control system to detect flow. The minimum flow may be adjusted by vertically adjusting the position of the photodetector.

In some embodiments, the end of the exhale cycle may be detected by a lack of bubbles in the PEEP-setting water container system (e.g., pressure-maintaining subsystem 20 in FIG. 2), for example, using an electric eye as described above.

Figure 15:
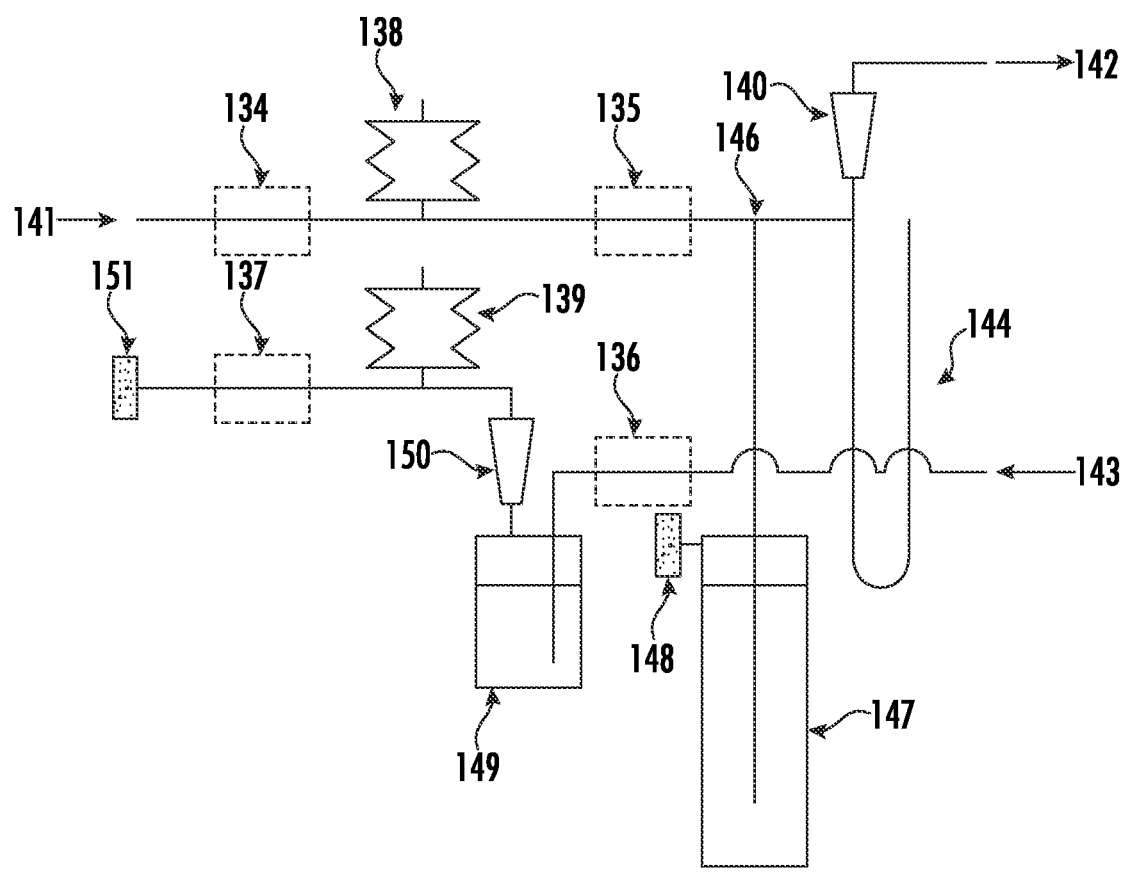
FIG. 15 is a simplified schematic of an example of a complete gas manifold (e.g., airway) of a ventilator system, in accordance with some embodiments.

FIG. 15 is a simplified schematic of an example of a complete gas manifold (e.g., airway) of a ventilator system, without valves, in accordance with some embodiments. Gas (e.g., air, or oxygen mixed with air) enters at 141 into tubing 146. The manifold may be a rigid fixed unit, where all subsystems and components are fixed in place with respect to each other, for example mounted on a rigid plastic plane. The manifold as a unit can be placed into the base ventilator unit containing the valves, control unit, electric eyes, and an adjustment interface and mechanics. Sections of tubing 134, 135, 136, and 137 are inserted into the pinch valves (e.g., as shown in FIGS. 3A-7). The expandable containers are 138 and 139 (e.g., as shown in FIGS. 10-12). A first portion of flow sensor 140 and a first portion of flow sensor 150 are included in the manifold, and a second portion of each of the flow sensors (e.g., the electric eyes) are located in the base ventilator unit (e.g., as shown in FIG. 14). A portion of a pressure sensor includes manometer 144 (e.g., as shown in FIGS. 13A-13C). The PIP is set by maximum-pressure unit 147 (e.g., as shown in FIGS. 8-9), with excess gas exited through filter 148 to atmosphere. The gas exits to the patient at 142. Gas exhaled from the patient enters at 143. The minimum-pressure maintaining subsystem 149 (PEEP) (e.g., as shown in FIG. 8) is in series with the flow sensor 150 (e.g., as shown in FIG. 14) which exits to bellows 139 (e.g., as shown in FIGS. 10-12) which can measure the exhaled tidal volume. Exhaled gas may then exit through filter 151 to atmosphere.

Figure 16:
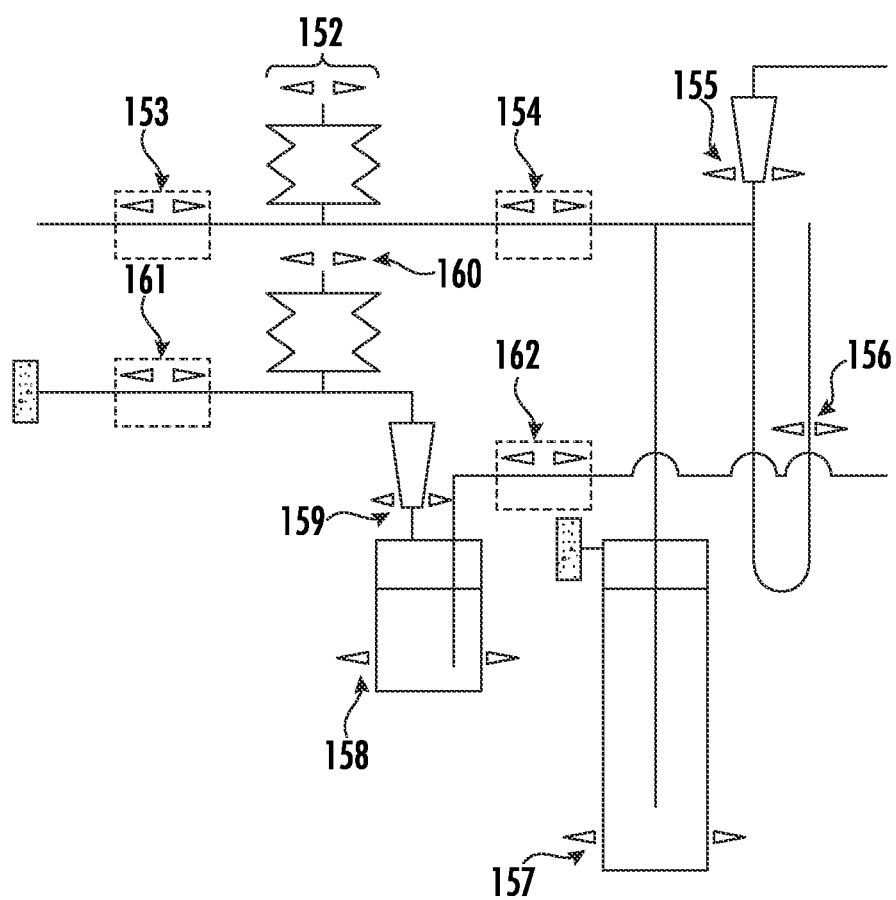
FIG. 16 is a simplified schematic of an example of the complete gas manifold in FIG. 15, including portions of the sensors in the manifold (e.g., airway) and the electric eye portions of the sensors located in the ventilator base unit, in accordance with some embodiments.

FIG. 16 is a simplified schematic of an example of the complete gas manifold in FIG. 15, including portions of the sensors in the manifold (e.g., airway) and the electric eye portions of the sensors located in the ventilator base unit, in accordance with some embodiments. The portions of the sensors located in the ventilator base unit are electric eyes 153, 154, 155, 156, 157, 158, 159, 160, and 161, and each include a light source and a light detector that may be mounted on the base ventilator unit. Electric eyes 153, 154, 161, and 162 are for valve positioning of a rotary actuator. Electric eyes 152 and 160 are for detecting a volume in the bellows. Electric eyes 155 and 159 are portions of the flow sensors in conjunction with the portion of flow sensor 140 and 150 (e.g., containing the container and ball shown in FIG. 14). Sensors 157 and 158 are portions of flow sensors (in conjunction with the container, liquid and tube of the maximum-pressure unit 147, and the minimum-pressure maintaining subsystem 149) that detect flow into the pressure relief traps. Electric eye 156 detects negative pressure for triggered breathing mode in conjunction with the manometer 144. The valves of the systems shown in FIGS. 15 and 16 may be configured to variably adjust the flow of gas through the valves (i.e., through a tube passing through each of the valves, or through a compressible section of a tube passing through the valve), as described herein.

In some embodiments, all measurements from the sensors in the ventilator unit are converted into an interrupt of an electric eye. This can simplify development and integration, as well as supply chain management and assembly, and may also reduce the cost of the system. In some cases, the sensors in the ventilator systems described herein use an "electric eye."

Figure 17A:
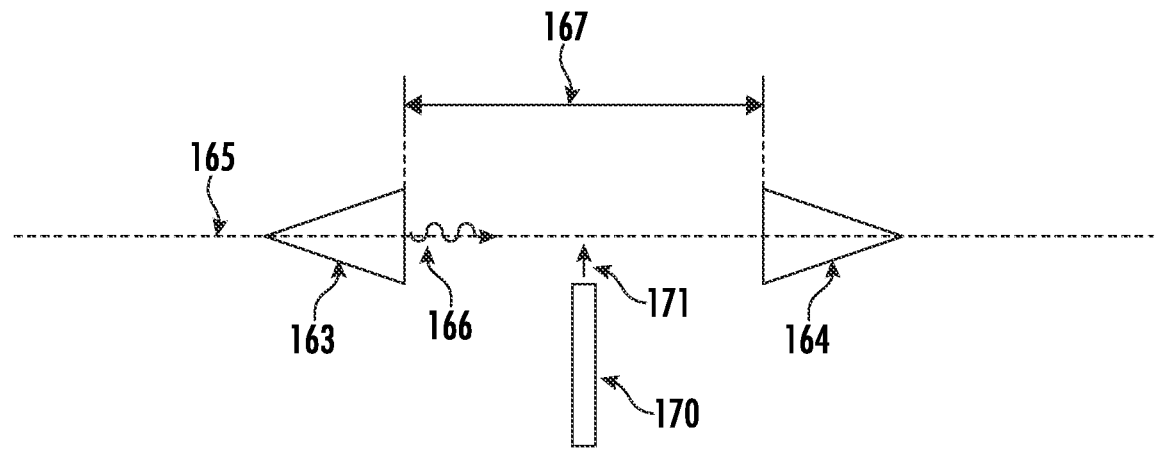
FIGS. 17A-17B are simplified schematics of examples of electric eyes, in accordance with some embodiments.
Figure 17B:
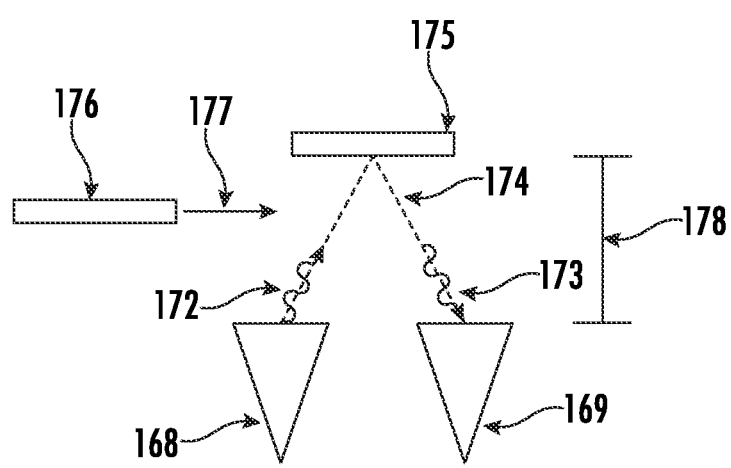

FIGS. 17A-17B are simplified schematics of examples of electric eyes, in accordance with some embodiments.

The electric eye in FIG. 17A includes light source 163 emitting light 166 (generally along line 165) towards detector 164 at distance 167 apart such that a non-light-transmissive means 170 can interrupt the light by inserting it in the path of the light 166 (by moving the non-light-transmissive means 170 in direction 171).

Alternately, FIG. 17B shows an example where the light emitter and detector 168 and 160 are next to each other facing in the same direction towards a fixed surface 175 that reflects incoming light 172 along a path 174 to become outgoing light 173, where the fixed reflective surface is a distance 178 away from the emitter and/or detector. The fixed surface 175 may have a high reflectance and/or low absorption, and/or high specular reflectance, such as reflecting more than 30%, or more than 50%, or more than 80%, or from 10% to 100%, of the light 172 along path 174. A non-light-transmissive object 176 may interrupt the light path by being inserted in in the path 174 of the light (by moving the non-light-transmissive object 176 in direction 177), for example, by absorbing light 172 (or scattering light 172 away from the detector 169, or deflecting light 172 away from detector 169). In other cases, the fixed surface 175 has a low reflectance (and/or high absorption, and/or low specular reflectance) compared to the object 176 which may have a high reflectance, and when the object 176 moves in the path of the light, it reflects the light from emitter 168 to detector 169, and the intensity of light 173 detected by the detector 169 increases.

All ventilator parameters of the systems shown in FIGS. 15 and 16 are adjustable either electrically or mechanically. Delays between cycles which are related to the inhale:exhale time ratio, may adjusted by an input to a control system such as with a knob and a variable resistor. PIP may be adjusted, for example, by moving the maximum-pressure unit 147 (e.g., moving vessel 76 containing liquid 77) up and down, as described above. The PEEP may be adjusted similarly, for example, by adjusting the minimum-pressure maintaining subsystem 149 up and down, as described above. The tidal volumes on inhale and exhale may be adjusted by moving the electric eye sensor up and down, as described above. The minimum flow in sensors 140 and 150 maybe adjusted by moving the electric eye up and down, as described above. The triggered breathing pressure may be adjusted by a moving an electric eye sensor up and down, as described above. In some cases, all of these mechanical adjustments may include mechanisms that attach the part to be moved to a slider on a panel that can be adjusted by user. For example, the panel may have 7 user-adjustable sliders, one for each of the adjustments described above. In some cases, the panel also has two knobs to adjust delays relating to breathing rate.

The gas manifold of FIG. 15 may or may not be disposed of between patients. The manifold may be made of low cost plastic materials so that it is not costly to dispose of between patients. Liquid such as oil or water is used by the PIP and PEEP pressure traps and the manometer. In some cases, liquid containing vessels may have a removable lower section to allow filling or may have a fitting such as a luer fitting to allow filling.

In some cases, the electronics of the control system for the ventilator systems shown in FIGS. 15 and 16 has no microprocessor. In some cases, all functions may be hard-wired into an analog and/or digital circuit, such that the system has no software. This can be beneficial for safety testing and development cost.

In some cases, an operator uses the ventilator systems shown in FIGS. 15 and 16 by opening a door, inserting the manifold, and filling it with water in the correct places. The door may be located at the back of the unit opposite the control panel, where the control panel is coupled to the movable sensors. The operator may then close the door, and may attach the unit to a patient and a gas source. The ventilator may also include a means for generating a mixed gas (e.g., containing oxygen, nitrogen, and/or air) and adjusting $FiO_2$, such that the input gas may be pure $O_2$ mixed with another gas (e.g., air, or nitrogen). The PIP and PEEP vessels may connect to the rest of the system such as via snapping them into one or more holders that are connected to a slider for adjustment up and down on the control panel.

In some cases, the ventilator systems shown in FIGS. 15 and 16 may include a screen-type user interface (e.g., an LCD display). In some cases, the ventilator system may include an LED-based user interface (e.g., with a set of LED indicators, or a set of LEDs forming a display). In some embodiments, the interface displays the sequencing of the valves, and flow, and other sensor data from the electric eyes. Patient data may also be stored and output by the control system.

Figure 18:
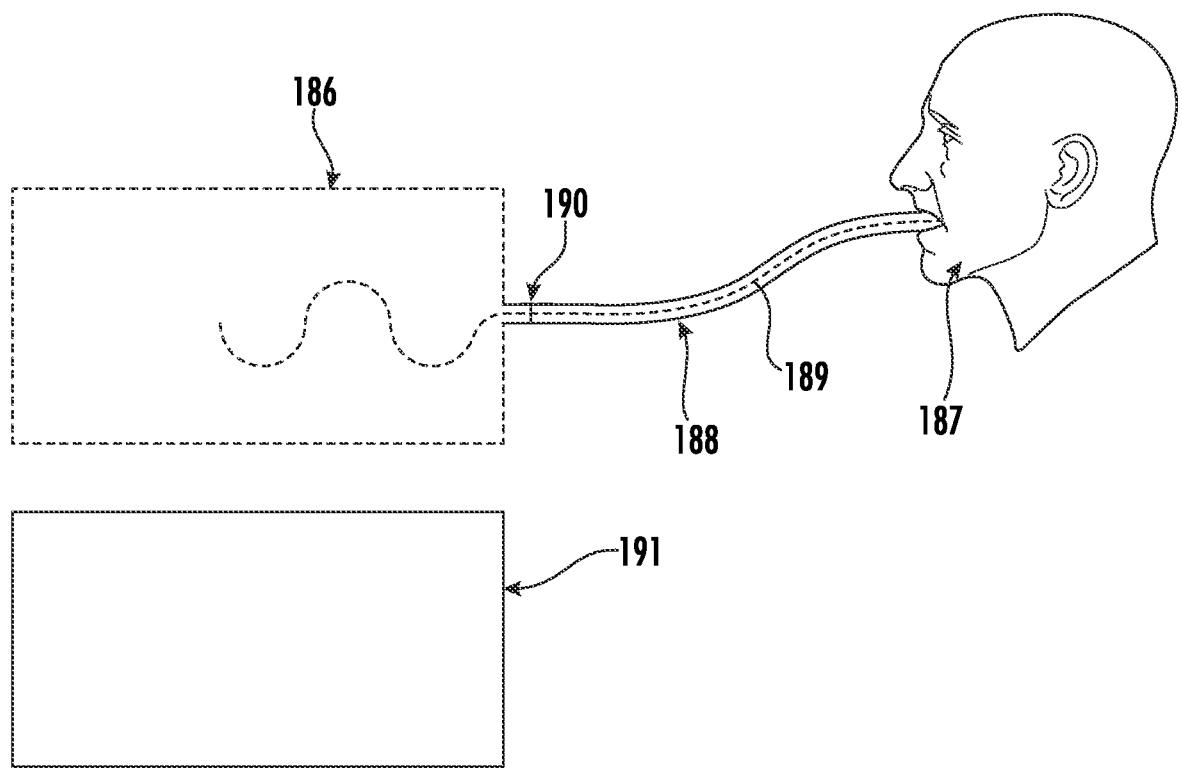
FIG. 18 is a simplified schematic of an example of a ventilator system, in accordance with some embodiments.

FIG. 18 is a simplified schematic of an example of a ventilator system, in accordance with some embodiments. A patient 187 is coupled by an air-conducting means (e.g., via a patient circuit 188) to a removable system (or removable unit) 186 via a connection 190. The removable system (or removable unit) 186 is inserted into the base unit 191, where the base unit contains some components of the ventilator system, such as valves and control system electronics. The contiguous path from the patient to the removable system is indicated by 189. In some embodiments, the air (or matter contained therein) that is exhaled from the patient 187 is contained within removable system (or removable unit) 186, such that at no point can the path 189 contact the base unit 191. That is, when the patient is coupled to the removable system (or removable unit) 186, there is no way for any air or matter to get from the patient to a surface of the base unit 191. In some cases, air or matter from a patient is confined within the removable system (or removable unit) 186, except for through one or more outlets (e.g., excess gas exit ports) to the atmosphere. In some cases, the air or matter from the patient passes through one or more filters before leaving an exit port to the atmosphere. In some cases, the exit ports are dedicated exit ports, wherein the exit port is used to expel excess gas to the atmosphere and is not used for any other function (e.g., as a sensor port). In some cases, air (or air with additional gases and/or matter) within the removable airway does not contact any portion of the base unit without first exiting the removable airway through a (filtered) exit port (e.g., a dedicated exit port, as described herein). Additionally, in some cases, all of the valve components are contained in the base unit, and no valve components can contact the air (or matter contained therein) that is exhaled from the patient 187.

In some cases, the air from the patient may contact the removable system (or removable unit) 186, and air from the patient may contact a portion of the base unit 191, as long as any contamination on the portion of the base unit 191 cannot be introduced back into the removable system (or removable unit) 186 (or a second removable unit that replaces removable system (or removable unit) 186 after removable system (or removable unit) 186 is removed from the base unit 191). In other words, any possible contamination on the base unit 191 cannot cross-contaminate a removable unit.

In some cases, a patient is a person or animal coupled to the ventilator via breathing tubes.

Figure 19:
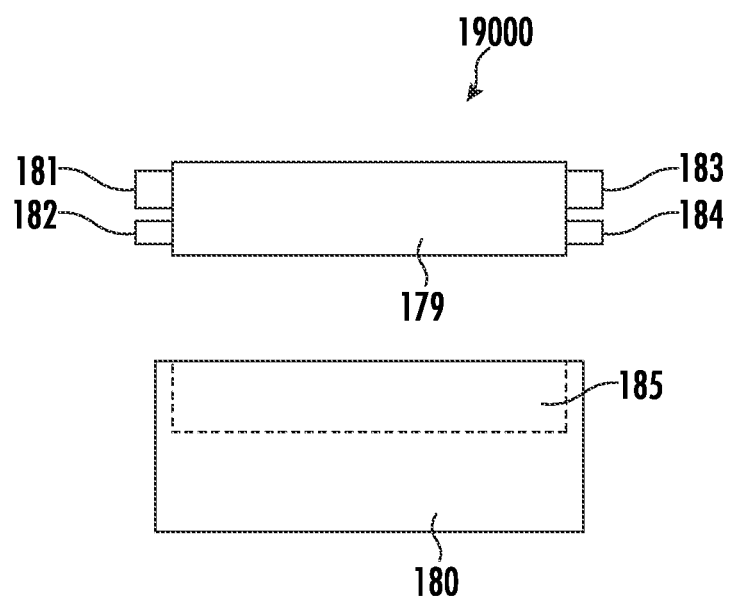
FIG. 19 is a simplified schematic of an example of a ventilator system, in accordance with some embodiments.

FIG. 19 is a simplified schematic of an example of a ventilator system 19000, in accordance with some embodiments. Ventilator system 19000 includes a removable system (or removable airway) 179 and a base unit 180. The removable system (or removable airway) 179 may be referred to as an airway, or a removable airway throughout this disclosure. Removable system (or removable airway) 179 may have 2, or 3, or 4, or more than 4 openings (or ports). In some cases, all of the openings to the removable system (or removable airway) 179 are used to either insert air into removable system (or removable airway) 179, or remove air from removable system (or removable airway) 179, and none of the openings to the removable system (or removable airway) 179 are used for any other purpose (e.g., as a sensor port). The removable system (or removable airway) 179 in this example has four ports that are used to insert or remove air from the removable system (or removable airway) 179, and are not used as sensor ports. For example, opening or port 181 can be used for an air supply, opening or port 182 can be used for an air exhaust, opening 183 can be coupled to a patient for inhalation, and opening 184 can be coupled to the patient for exhalation.

In another example, removable system (or removable airway) 179 only has two ports 181 and 183. In this example, opening or port 181 can be used for an air supply and an air exhaust. This may require external valving of the air supply to alternately connect to the air supply and an air exhaust (which could be atmosphere or a contained system). A connection to the patient can then be made through a single port 183 for inhalation and exhalation. This embodiment may require internal valving to direct supplied air to the port during inhale and to direct exhausted air to the exhaust during exhale.

The removable system (or removable airway) 179 may be inserted or generally fixedly placed in connection with the base unit 180 in a region 185 of the base unit, such a docking station. In some cases, there are structures (e.g., guide pins, guide slats, guide holes, guide slots, or structures shaped like opposing puzzle pieces) to assist with aligning the removable system (or removable airway) 179 with the base unit 180. The removable system (or removable airway) 179 may be larger or smaller than region 185 of the base unit. For example, removable system (or removable airway) 179 may be larger than region 185, and the inlets and outlets of removable system (or removable airway) 179 may extend past the boundaries of region 185. In another example, removable system (or removable airway) 179 may be smaller than region 185 such that removable system (or removable airway) 179 fits within region 185. In such cases, the ports (i.e., the inlets and outlets) of removable system (or removable airway) 179 may include bent (e.g., 90 degree) sections such that connections may be made to the ports of the removable system from above.

The removable system (or removable airway) 179 may be configured to be removable from the base unit 180. Removable system (or removable airway) 179 may be removed to be cleaned or to be disposed of and subsequently replaced with a new removable system (or removable airway) 179 or a cleaned removable system (or removable airway) 179.

The removable system (or removable airway) 179 may further be configured to be cleaned in place (e.g., the removable system (or removable airway) 179 may be configured to be removable and cleaned in place, or the system may not be configured to be removable). The capability to be cleaned may be enabled by the isolation of the airway from the base unit, and its size and shape as described above.

In some embodiments the isolated removable system (or removable airway) 179 is removable. In some embodiments, the removable system (or removable airway) 179 is disposable (e.g., between patients). In some embodiments, the removable system (or removable airway) 179 is cleanable. These embodiments are not mutually exclusive.

In some embodiments, the removable system (or removable airway) 179 may contain sensors. Sensors may be for pressure and or flow. The sensors may be active, such as powered by electricity. If the removable system contains sensors, then the removable system may have connectors on the removable system that mate to connectors on the base unit 180. The connectors may be electrical. Electrical connections may also be non-contact. Power to the sensors may be wireless such as by the Qi standard or other radiative or inductive means. Communication to the sensor may be wireless or wired, such as by WiFi or Bluetooth.

In some embodiments, the removable system (or removable airway) 179 may have regions or systems that together with a related system in the base unit 180 form a sensor system. In some embodiments, the regions or systems in the removable unit are passive, in that they do not contain any active components, such as electronics or sensors that receive electrical power.

Figure 20:
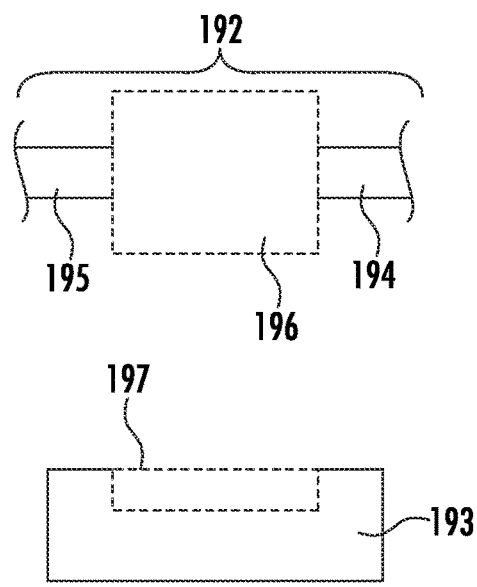
FIG. 20 is a simplified schematic of an example of a sensor with portions in the removable system and in the base unit, in accordance with some embodiments.

FIG. 20 is a simplified schematic of an example of a sensor with portions in the removable system (e.g., removable system (or removable airway) 179 in FIG. 19) and in the base unit (e.g., 180 in FIG. 19), in accordance with some embodiments. In FIG. 20, subsystem 196 of the removable unit 192 forms a first portion of a sensor. Subsystem 196 has inlet 194 and outlet 195 that couple the subsystem 196 to other components of the removable system. Subsystem 197 in a base unit 193 forms a second portion of the sensor such that the two subsystems form a sensor system. That is, the subsystems 196 and 197 together form a sensor, for example, to measure pressure and/or flow. The method of interaction between the two subsystems 196 and 197 may be electrical, optical, mechanical, or other means of interacting. Each subsystem 196 and 197 comprises components which on their own do not function as a sensor, but when combined form a system that is able to sense a desired property. A sensor can have an output signal that is predictably related to a property (e.g., pressure or flow) of a system. The output signal may be electrical (either analog or digital), optical or mechanical.

In some embodiments, the subsystem 196 in the removable unit 192 has a means for allowing light to enter the airway, such as a transparent window, such as glass, quartz, or plastic, or an optical filter or lens. The subsystem 196 may also have a plurality of windows or other passive optical components such as mirrors, lenses, and gratings.

In some cases, the complexity of the removable unit 192 (or removable system (or removable airway) 179 in FIG. 19) is minimized, for example, to minimize cost of a potentially disposable removable unit.

Active components such as pressure and flow sensors may be incorporated into subsystem 196. For example, a heat source (e.g., a hot wire) and a temperature sensor (e.g., a thermistor) may be disposed in subsystem 196, and subsystem 196 may have external electrical connections to a mating part on the base unit, to enable what is generally known as hot-wire anemometry. In another example, pressure sensors (e.g., MEMS sensors) may also be disposed in subsystem 196, and subsystem 196 may have external electrical connections that mate to a base unit.

In some embodiments, ultrasonic flow sensors may be arranged to measure flow within the airway in the removable unit. In some embodiments using ultrasonic flow sensors, there are no active components in the subsystem 196. The subsystem 196 may contain tubing, and optionally a means (e.g., a slot, or a pin, or other alignment structure) to fixedly couple subsystem 196 to the ultrasonic source and sensors in the base unit 193. The tubing may be metal, plastic, or other suitable material for transmitting ultrasound.

In yet another embodiment, flow within subsystem 196 (that is part of removable unit 192) may be measured with optics in the subsystem 197 (that is part of the base unit 193) such as by interferometry or by a Schlieren-type shadowgram (e.g., using Schlieren photography, or shadowgraphs). Such systems measure flow that is related to disturbances in the airway such as turbulence or induced Karman vortices. Such sensors could include an optical system (e.g., including a light source and a detector, where the detector is an array of photodetectors, or a camera (e.g., a CCD camera)) in the subsystem 197, and one or more windows for light to enter and exit an airway within subsystem 196 containing a flowing gas, as described herein.

In yet another embodiment, flow may be measured by a mechanical means in the subsystem 196, such as using a paddle wheel or turbine. Air flow makes the wheel or turbine rotate. The movement of the paddle wheel or turbine can be measured by external (e.g., in the subsystem 197) light source and detector means (e.g., an electric eye, as described herein), whereby the paddle wheel interrupts of changes the intensity of the light impinging upon a part of the rotating part such that a detector disposed to receive light measures a change in intensity as the rotating part moves. The light may be reflected, refracted, diffracted, or pass through in such a position that it is interrupted and then not interrupted periodically. The rate of the changes in intensity correspond to the speed of the rotating means and the flow rate.

In some embodiments, pressure may be measured by deformation of a surface of the airway in subsystem 196. The deformation may occur within a region that has a lower compliance than the surrounding region enclosing the airway such that when the pressure in the airway increases, the softer (or compliant) region pushes outwards.

Figures 21A, 21B:
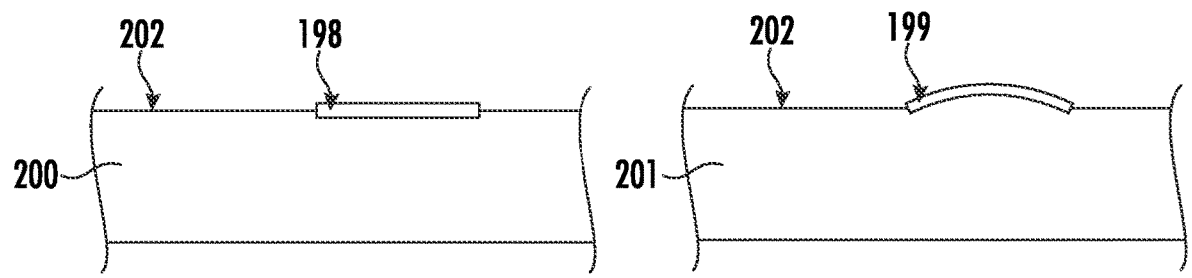
FIGS. 21A-21B are simplified schematics of an example of an airway with a compliant region, in accordance with some embodiments.

FIGS. 21A-21B are simplified schematics of an example of an airway with a compliant region, that can be a component of subsystem 196 in some embodiments. In FIG. 21A, an airway 202 contains a compliant region 198. When pressure 200 is the same inside and outside the airway, the region 198 is in a relaxed state (e.g., flat, or other geometries). When the pressure 201 is greater than the pressure outside the airway (generally atmospheric pressure), the region 199 (or a portion of region 199) distorts. This distortion can be measurable using different means of measuring a change of the compliant region, such as optically, electrically, and or mechanically. For example, the distortion could be measured by bouncing a light source off the distorted region and detecting a change in the magnitude or position of the reflected light. In another example, the distortion could be measured by detecting a change in capacitance between an electrically conductive portion of the distorted region and a second electrically conductive surface, that is fixed in a proximity to the electrically conductive portion of the distorted region 199. The configuration of the electrically conductive portion of the distorted region 199 and the second electrically conductive surface can be configured such that a desired change in pressure is sufficient to cause a measurable change in capacitance. In another example, the distorted region 199 could be measured electrically such as by coupling a strain gage to the distorted region, and coupling electrical connections from the strain gage to a means to detect a change (e.g., in resistance) of the strain gauge. Other strain gauges such as fiber optic strain gauges may also be used to detect the distortion of region 199. In some cases, the deformable region 198 may contact a mechanical pressure gage, such as the surface of a Bourdon tube.

Figure 22A:
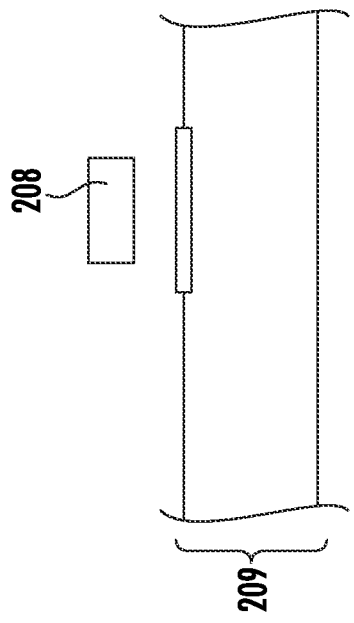
FIGS. 22A-22B are simplified schematics of an example of a pressure sensor, in accordance with some embodiments.
Figure 22B:
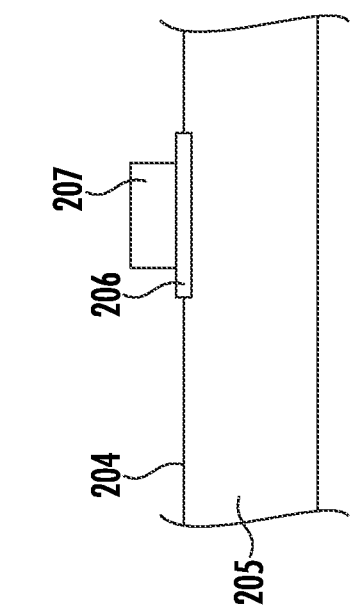

FIGS. 22A-22B are simplified schematics of an example of a pressure sensor, in accordance with some embodiments. In FIG. 22A, the compliant region 206 contacts a force-measuring means 207 that may be a component of the subsystem 197. That is, the force-measuring means 207 may be part of and fixed within the base unit 193. When the subsystem 196 is removed, the subsystem 209 (corresponding to subsystem 196) is removed and is no longer in contact with the force-measuring means 208 (corresponding to subsystem 197). When the pressure 205 increases beyond atmospheric pressure the region 206 presses on the force-measuring unit 207. The force measured by the force-measuring unit 207 can be calibrated to read out in any unit system (e.g., by a control system), such as cmH$_2$O. The force-measuring unit 207 may contain a strain gage as in a scale system, or other load cell. The force-measuring unit 207 may be placed in contact with the compliant region 206 such that at equilibrium pressure between the inside and the outside of the airway, a positive force is measured by force-measuring unit 207. In some cases, force-measuring unit 207 may be coupled (e.g., reversibly so it may be decoupled when the removable unit is removed, for example, using a magnetic coupling, an electromagnetic coupling, a clip, a pin and an eye hole, an adhesive, or other reversible mechanical connection means) to compliant region 206, such that negative pressure inside the airway with respect to outside the airway may be measured. In some cases, force-measuring unit 207 may be coupled to compliant region 206, and be a part of subsystem 196. In some cases, a negative pressure inside the airway with respect to outside the airway may be measured using light (e.g., using a light source and detector that are part of the base unit 193) to detect the movement of compliant region 206, as described herein.

Figure 23A:
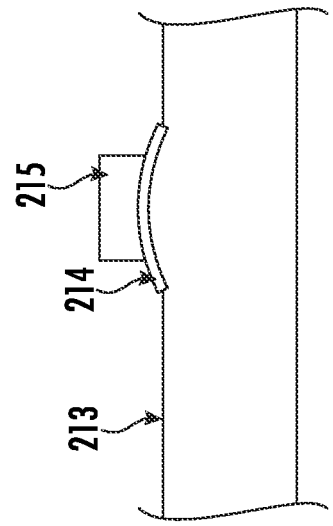
FIGS. 23A-23B are simplified schematics of an example of a pressure sensor, in accordance with some embodiments.
Figure 23B:
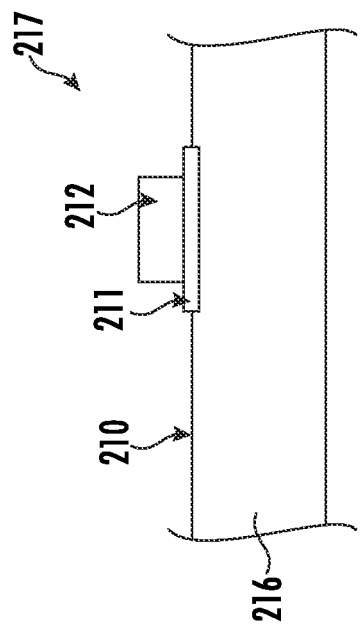

FIGS. 23A-23B are simplified schematics of an example of a pressure sensor, in accordance with some embodiments. In FIG. 23A the pressure 216 inside tube 210 is the same as pressure 217 outside tube 210. Deformable region 211 is approximately flat, or undeformed, in this example, but may have other shapes in this equilibrium condition. A portion of a load cell (or other force sensing means) 212 is in contact with the deformable region 211 at the position shown. FIG. 23B shows the case where the pressure inside the tube is higher than the pressure outside the tube, where the deformable region 214 expands outward, pressing on the load cell (or other force-sensing means) 215. FIG. 23B shows the load cell (or other force-sensing means) 215 moving to a new position, where the position is measured by the force-sensing means. This measurement can be converted to a pressure in desired units. The force versus pressure may not be linear. In such a case, a system may have a look-up table or other means of storing the relationship between force and pressure such as by a curve fit formula to convert the measured force to a pressure.

In some embodiments, flow of a gas (e.g., air, or oxygen mixed with other gases, or a gas with other materials such as solid or liquid particles) within a removable airway (e.g., 192 of FIG. 20) can be measured using sound produced by the moving gas.

In some embodiments, the gas flow within a removable airway (e.g., 192 of FIG. 20) can be measured by detecting the level of sound made by the gas (e.g., air) moving in the tube. In general, the microphone (used as a term for a sensor that converts sound waves to an electrical signal, or to another detectable signal that is not sound, such as to light) is completely outside the tube and is contained in the subsystem 197.

Figure 24:
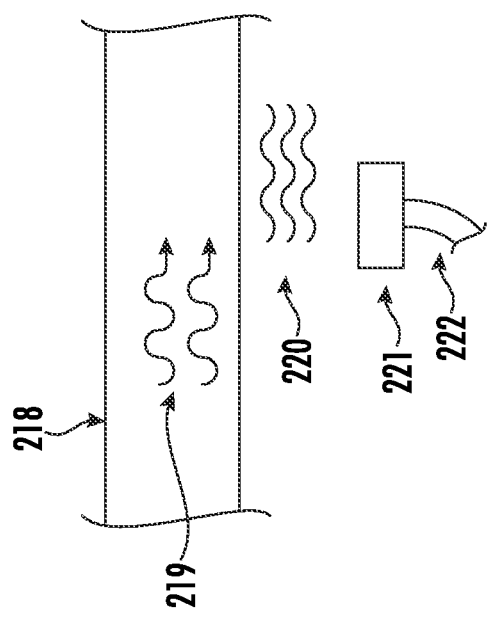
FIG. 24 is a simplified schematic of an example of a flow sensor contained within the base unit, in accordance with some embodiments.

FIG. 24 is a simplified schematic of an example of a flow sensor contained within the base unit (e.g., 180 in FIG. 19), in accordance with some embodiments. A tube 218 (e.g., that is part of removable system (or removable airway) 179 in FIG. 19) may have a gas (e.g., air) 219 flowing in it. The gas causes a sound 220 to be emitted from the tube, detectable outside the tube via a microphone 221, which converts the sound 220 to an output signal on the wires 222. The output signal can then be provided to a control system (as described herein) for controlling different components (e.g., valves configured to variably adjust the flow of gas through the valve) of the ventilator.

In some cases, the tube 218 may be a portion of the flow sensor that is a part of the removable system (e.g., removable system (or removable airway) 179 in FIG. 19), and microphone 221 is a portion of the flow sensor that is a part of the base unit (e.g., 180 in FIG. 19). For example, tube (or section of tube) 218 may be configured to permit sound to pass through a wall of the tube, such that the sound generated by the flowing gas within the tube may be efficiently transferred to microphone 221 located outside of tube 218. Tube 218 may be configured to permit sound to pass through a wall of the tube, for example, by tube 218 being made of a material that allows sound to pass through it (e.g., silicone, vinyl, plastic, or metal), and/or by including structures within tube 218 that increase the intensity of sounds generated by a flowing gas. Additional examples of acoustic flow sensors with portions that are part of the removable system (e.g., removable system (or removable airway) 179 in FIG. 19) and that are part of the base unit (e.g., 180 in FIG. 19) are described herein.

Figure 25:
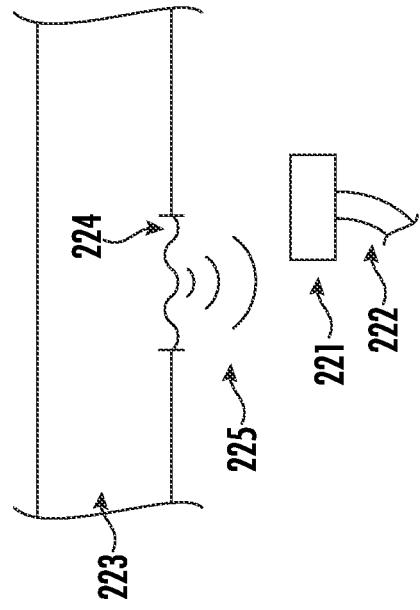
FIG. 25 is a simplified schematic of an example of a flow sensor with portions that are part of the removable system and that are part of the base unit, in accordance with some embodiments.

FIG. 25 is a simplified schematic of an example of a flow sensor with portions that are part of the removable system (e.g., removable system (or removable airway) 179 in FIG. 19) and that are part of the base unit (e.g., 180 in FIG. 19), in accordance with some embodiments. The wall of the tube 223 may have a region (or diaphragm) 224 that is of a material disposed to transmit sound 225 more easily than the walls of the tube. Tube 223 and region 224 may be part of a removable system (e.g., removable system (or removable airway) 179 in FIG. 19). This region 224 in may be a thin diaphragm (e.g., made of plastic). Such a diaphragm 224 may be similar to those found on the faces of stethoscopes or speakers. The diaphragm 224 is fixed around its edges to the tube 223. In some cases, tube 223 may have a flat region adjacent to diaphragm 224, such that diaphragm 224 may have a circumference that lies in a flat non-curved plane. The diaphragm 224 may also be curved or have undulations in it (e.g., allowing for greater movement). The sound emitted from the diaphragm 224 can then be detected using microphone 221, which converts the sound 225 to an output signal on the wires 222, as described above.

In other embodiments, the flow rate within tube 223 may be detected by placing an accelerometer (not shown) against the diaphragm 224. The support and connection to the base unit would generally have a lower compliance than the diaphragm.

Figure 26:
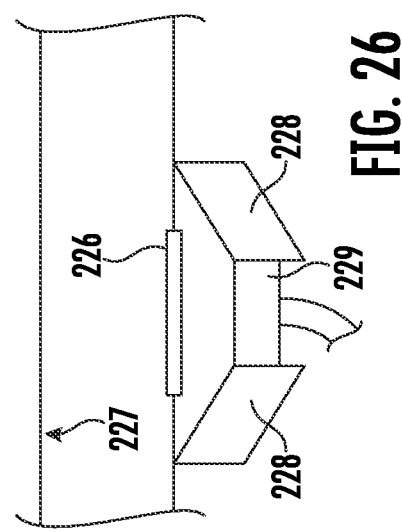
FIG. 26 is a simplified schematic of an example of a flow sensor with portions that are part of the removable system and that are part of the base unit, in accordance with some embodiments.

FIG. 26 is a simplified schematic of an example of a flow sensor with portions that are part of the removable system (e.g., removable system (or removable airway) 179 in FIG. 19) and that are part of the base unit (e.g., 180 in FIG. 19), in accordance with some embodiments. FIG. 26 shows the microphone 229 in the base unit (e.g., corresponding to subsystem 197) enclosed in a cone 228. The cone 228 may contact the tube 227 and surround the sound-transmitting region (e.g., diaphragm) 226. In some cases, the tube 227 is not mechanically connected to the sound gathering means (or cone) 228 cone and microphone 229. Thus, the tube 227 may be separated from the sound detecting means (228 and 229), and subsequently the same (or similar) tube 227 be placed back in contact with the sound detecting means (228 and 229). In a ventilator, the sound detecting system (228 and 229) may be part of the base ventilator unit and the tube is part of the disposable airway system.

Figure 27:
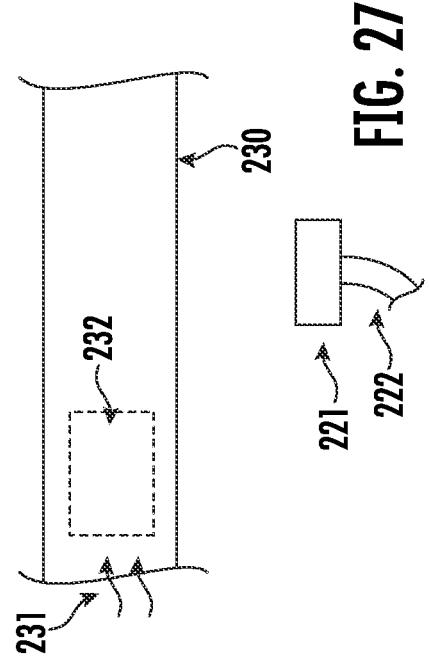
FIG. 27 is a simplified schematic of an example of a flow sensor with portions that are part of the removable system and that are part of the base unit, in accordance with some embodiments.

FIG. 27 is a simplified schematic of an example of a flow sensor with portions that are part of the removable system (e.g., removable system (or removable airway) 179 in FIG. 19) and that are part of the base unit (e.g., 180 in FIG. 19), in accordance with some embodiments. A tube 230 may also have disposed within it or as a part of it as a system, a sound generating subsystem 232, which has gas (e.g., air) 231 impinging upon it. The sound generating subsystem 232 is designed to generate sound when gas 231 impinges on it, converting some of the energy of the flowing gas 231 to sound. This may have the beneficial effect of increasing the amount of sound generated in tube 230 for detection. The sound emitted from the sound generating subsystem 232 can be detected using microphone 221, as described above.

Figure 28:
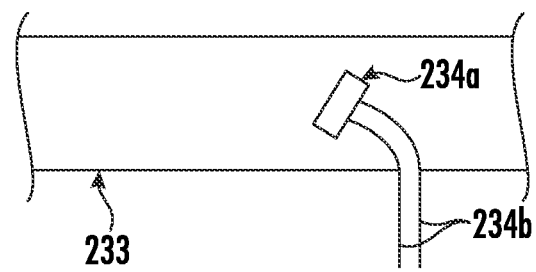
FIG. 28 is a simplified schematic of an example of a flow sensor that is contained within the removable system, in accordance with some embodiments.

FIG. 28 is a simplified schematic of an example of a flow sensor that is contained within the removable system (e.g., removable system (or removable airway) 179 in FIG. 19), in accordance with some embodiments. In FIG. 28, microphone 234a may be disposed within the tube 233 that is part of the removable system. In some cases, wires 234b carrying an output signal from the microphone pass in a sealed fashion through the walls of the tube 233 to connect with a control system that can display or otherwise make use of the sound output signal (as described herein).

Figure 29:
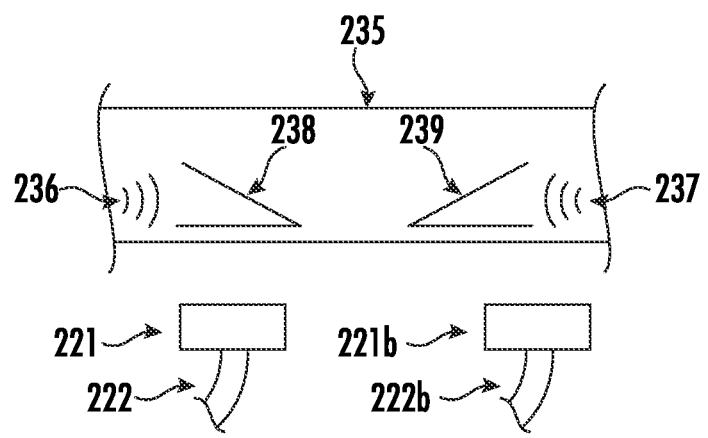
FIG. 29 is a simplified schematic of a flow sensor that is a part of the removable system, or with portions that are part of the removable system and the base unit, in accordance with some embodiments.

FIG. 29 is a simplified schematic of a flow sensor that is a part of the removable system (e.g., removable system (or removable airway) 179 in FIG. 19), or with portions that are part of the removable system (e.g., removable system (or removable airway) 179 in FIG. 19) and the base unit (e.g., 180 in FIG. 19), in accordance with some embodiments. FIG. 29 shows a flow detector system with more than one microphone (2 in this case, but there could be more than 2 in other cases), such that flow in different directions may be detected differently thus indicating flow direction. A tube 235 may have a first structure 238 and a second structure 239. In some cases, structures 238 and 239 are microphones, where microphone 238 may be more sensitive to sound 236 coming from a direction opposite to a sound 237 which may be more easily detected by a microphone 239. The microphones may be placed in any direction which enables them to have an asymmetric sensitivity to flow direction.

FIG. 29 also shows microphones 221 and 221b, that are located outside of tube 235, and may be the base unit (e.g., 180 in FIG. 19). In some cases, structures 238 and 239 are sound generating subsystems (e.g., subsystem 232 in FIG. 27). These sound generating structures 238 and 239 may be disposed to generate sound from flow more from one direction than another, and microphones 221 and 221b can be used to detect the direction of the flow. Sound generating structures 238 and 239 may also generate different sounds, such as sounds of different frequencies, where one sound generator may generate a tone if gas (e.g., air) comes from one direction and a second sound generator generates a sound coming from the opposite direction with a different tone than the first generator and a single microphone (e.g., 221, located outside of the tube 235) which output a signal which can then be processed to determine the tone and in this way determine which generator produced the sound and thus which direction the flow was from. Such tones may also be proportional to flow, so the frequency (or ratio frequencies, or frequency spectrum) of the sound may be used to determine flow rate. The sound emitted from the sound generating subsystems 238 and 239 can be detected using microphones 221 and 221b, as described above.

Figure 30:
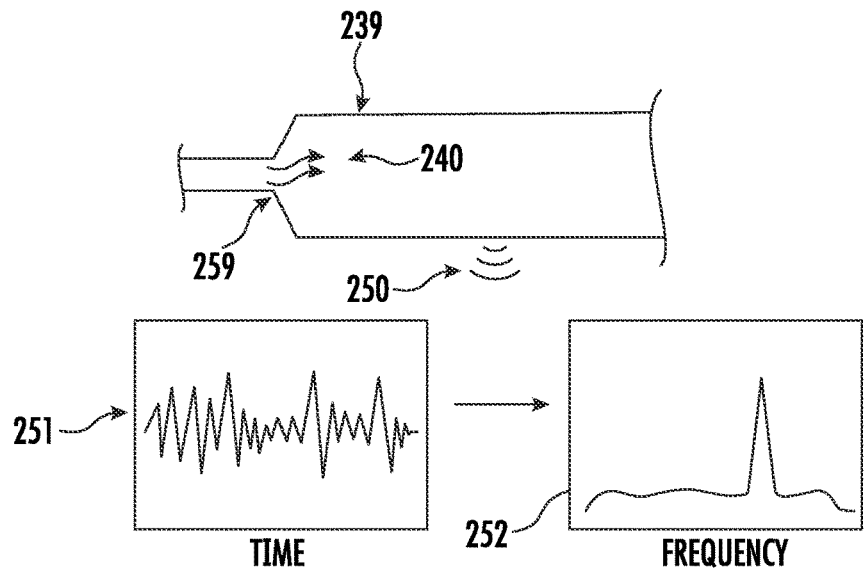
FIG. 30 shows a simplified schematic of an example of a structure within a tube that may generate sound that can be detected by a microphone of a flow sensor, and the frequency spectrum of the sound that is processed to determine a flow rate of the gas (e.g., air), in accordance with some embodiments.

FIG. 30 shows a simplified schematic of an example of a structure within a tube that may generate sound that can be detected by a microphone of a flow sensor, and the frequency spectrum of the sound that is processed to determine a flow rate of the gas (e.g., air), in accordance with some embodiments. The acoustic flow sensors described herein may detect sounds (generated by a flowing gas) in any frequency range where a microphone operates, for example from less than 100 Hz to greater than 20 kHz, or from 100 Hz to 20 kHz, or from 1 kHz to 20 kHz, or from about 20 kHz to about 40 kHz, or at about 10 kHz. The higher frequencies, such as those above 20 kHz, may be advantageous because there tends to be little ambient noise in this region so there is less ambient noise to interfere with the operation of the sensor. FIG. 30 shows a tube system through which gas (e.g., air) flows that may generate sounds which have a detectable harmonic content. That is, the sound may not be characterized as noise, such as white noise, but may have certain frequencies with an amplitude larger (or much larger) than the background. Orifice 259 is smaller than the tube 239 into which gas flows, which can preferentially generate certain sound frequencies. In this example, tube 239 with gas (e.g., air) 240 generates a sound 250 which has a trace versus time 251 with a frequency spectrum 252 where one or more peaks are present. The peaks in frequency may be detected and their amplitude correlated with flow rate, such as by taking a Fourier transform or other mathematical transform that converts from time domain to frequency domain, by the use of filters, or by a lock-in technique. The tube system may be designed to generate a specific frequency. Advantageously, the frequency would be a high frequency above where most ambient sounds are, such as in a hospital, where generally there is not much sound above 10 kHz or 20 kHz. Additionally, using an orifice 259 may generate greater sound levels for the same flow rate than tubes without such an orifice 259.

Alternatively, a subsystem such as 232 in FIG. 27 could preferentially generate sounds at certain frequencies, and the sound can be analyzed in the frequency spectrum as described above, to make the flow detector less susceptible to errors caused by ambient noise. For example, the subsystem 232 in FIG. 27 may be a reed or a whistle. A reed used in the flow sensors described herein may be a structure designed to vibrate when gas (e.g., air) passes over it, such as in a clarinet, thus transducing flow energy to sound energy. In some cases, a flow sensor described herein may use two or more, or a plurality of, reeds. The two or more reeds may generate the same tone spectrum or different tone spectrums, or generate different tones at different flow rates. The sound generating subsystem 232 may also be a whistle (e.g., a structure that passes flowing gas (e.g., air) across its own path to create a resonance which is a vibration of compression in the gas which is converted to sound).

Figure 31A:
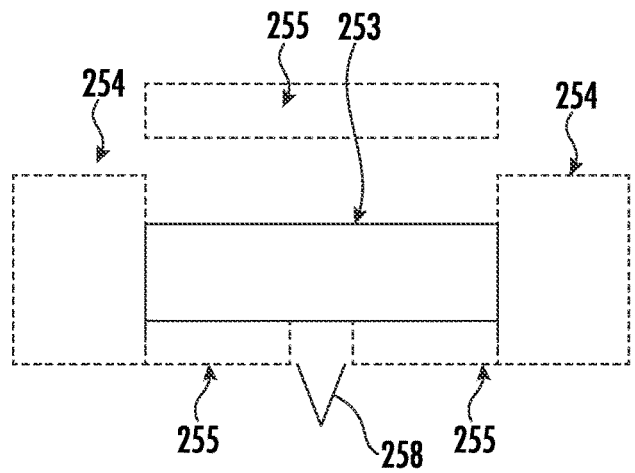
FIGS. 31A-31B are simplified schematics of a flow sensor with portions that are part of the removable system and the base unit, in accordance with some embodiments.
Figure 31B:
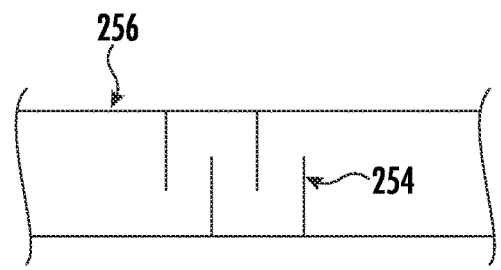

FIGS. 31A-31B are simplified schematics of a flow sensor with portions that are part of the removable system (e.g., removable system (or removable airway) 179 in FIG. 19) and the base unit (e.g., 180 in FIG. 19), in accordance with some embodiments. FIG. 31A shows a flow sensor including regions 254 and 255 surrounding the flow detection region within tube 253, and microphone 258. Regions 254 and 255 may include one or more structures that insulate the sound detection region from sound sources external to the sound detecting region. For example, a structure in regions 255 may include sound insulating materials such as fiberglass insulation, STYROFOAM™, polymer foams, metals, or laminates (e.g., having alternating impedance to sound transmission). FIG. 31B shows an example of a region 254. In some cases, regions 254 may include a tube 256 (that couples with tube 253 in FIG. 31A) and structures (e.g., baffles) 257 in a zigzag pattern, that can block sound yet still let gas (e.g., air) flow freely. In some cases, the microphone 258 may also be insulated with materials and/or structures (not shown) from sound sources external to the sound detecting region. The regions 254 and/or 255 may be part of the removable system (e.g., removable system (or removable airway) 179 in FIG. 19) and/or part of the base unit (e.g., 180 in FIG. 19). The tube may include a diaphragm (not shown) that is part of the removable system (e.g., removable system (or removable airway) 179 in FIG. 19). The microphone 258 may be part of the base unit (e.g., 180 in FIG. 19), or may be affixed to and be a part of the removable system (e.g., removable system (or removable airway) 179 in FIG. 19).

The microphone(s) of the flow detectors described herein (e.g., in FIGS. 14, and 20-33E) may have a gain that is adjustable in real time in response the changes in sound amplitude. In some embodiments, the gain is high for low levels of sound, and the gain is low for high levels of sound. In some embodiments, the output signal from the microphone has an approximately constant amplitude, and the gain is continually adjusted to keep the output signal amplitude approximately constant, such that the output signal is the gain, and the gain is then correlated with sound level. In this manner, a microphone used in the flow sensors described herein may have an increased dynamic range.

In a ventilator, the flow rate detected is generally in the range of less than 1 liter per minute up to 60 liters per minute, or up to 100 liters per minute. Flow detection by sound can be very sensitive compared to turbines or hot wire anemometers, with a fast response times as well. Flow rates may be detectable at 0.1 liters per minute in tubes of generally about 25 mm diameter. This is a very slow movement of gas, of about 3 mm per second. Further, in the flow region of 10-50 liters per minute or 1-60 liters per minute, the flow rate versus amplitude of sound generated may be approximately linear (in some tubes). In some cases, the amplitude of sound generated decreases above a certain flow rate, which may also be advantageously used to detect a certain flow rate with a high sensitivity as the fall off is greater than the rise at lower flow rates.

Figure 32:
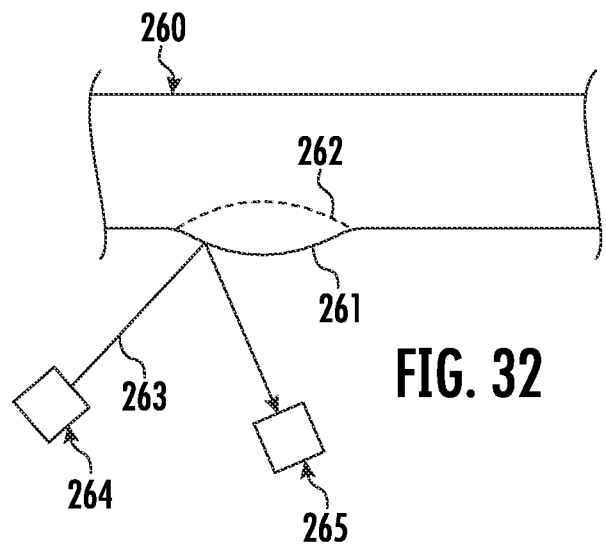
FIG. 32 is a simplified schematic of an example of a flow sensor with portions that are part of the removable system and the base unit, in accordance with some embodiments.

FIG. 32 is a simplified schematic of an example of a flow sensor with portions that are part of the removable system (e.g., removable system (or removable airway) 179 in FIG. 19) and the base unit (e.g., 180 in FIG. 19), in accordance with some embodiments. FIG. 32 shows a flow sensor that uses optical means to detect sound generated in a tube. A tube 260 with gas flowing in it may cause a diaphragm 261/262 to vibrate between positions 261 and 262. A light beam 263 generated by a light source 264 may impinge upon the surface of the diaphragm and be reflected into a detector 265. The intensity and/or position of the beam at the detector may be transduced into a signal proportional to the sound or movement of the diaphragm, such as with a photodiode capable of measuring the intensity of the beam 263, or a light sensor capable of measuring the position of beam 263 (e.g., a split photodiode, array of photodiodes, or an image sensor such as a camera). The light source 264 may be a laser, an incandescent lamp, or an LED. The diaphragm 261/262 may be part of the removable system (e.g., removable system (or removable airway) 179 in FIG. 19), and the light source 264 and detector 265 may be part of the base unit (e.g., 180 in FIG. 19).

Figure 33A:
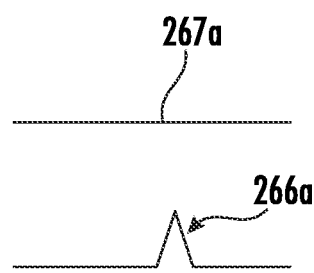
FIGS. 33A-33E are simplified schematics of portions of flow sensors that may be used in flow sensors that are contained in the removable system, or that have portions that are part of the removable system and the base unit, in accordance with some embodiments.
Figure 33B:
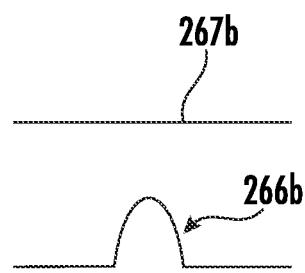
Figure 33C:
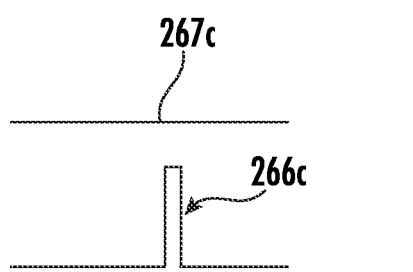
Figure 33D:
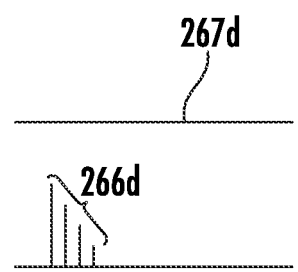
Figure 33E:
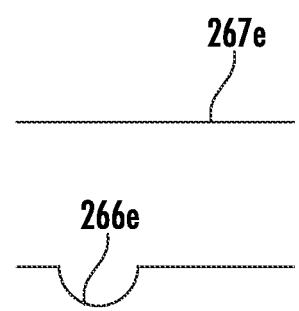

FIGS. 33A-33E are simplified schematics of portions of flow sensors that may be used in flow sensors that are contained in the removable system (e.g., removable system (or removable airway) 179 in FIG. 19), or that have portions that are part of the removable system (e.g., removable system (or removable airway) 179 in FIG. 19) and the base unit (e.g., 180 in FIG. 19), in accordance with some embodiments. The tube of a flow sensor, or a deformable region of the tube, may have shapes and geometries other than planar. For example, one or more structures may extend into the tube or protrude from the tube, such that flow within the tube impinges on the structure(s) and generates sound. FIGS. 33A-33D show examples of different structures 266a-e extending into or protruding from the tube 267a-e of a flow sensor. FIG. 33A shows a structure 266a that includes a pointed groove or conical indent extending into the tube 267a. FIG. 33B shows a structure 266b that includes a rounded indent extending into the tube 267b. FIG. 33C shows a structure 266c that includes a narrow indent (or pillar) extending into the tube 267c. FIG. 33D shows a structure 266d that includes a plurality of one or more rods or slats of the same or different geometries extending into the tube 267d. FIG. 33E shows a structure 266e that includes a region protruding from tube 267d. The tube may have a plurality of sound-generating structures (e.g., 266a-e as shown in FIGS. 33A-33C), and/or a plurality of microphones (not shown) to detect the sound from the structures 266a-e. The sound generating structure(s) (e.g., 266a-e) may be located within one or more sound generating regions of the tube (e.g., 267a-e). The sound generating region(s) may be in more than one location within the tube, and/or may surround the tube. The sound generating region(s) may be a section of the tube such as a thin section such that sound is emitted generally radially outwards all around the tube. A chamber may be disposed around the tube to collect sound from many directions emitted by the tube.

The flow detectors described herein (e.g., in FIGS. 14, and 20-33E) may be, or have portions that are, a stand-alone unit that can be connected to an inlet and an outlet tube or pipe.

The flow detectors described herein (e.g., in FIGS. 14, and 20-33E) may be a system that is, or have portions that are, fixedly couplable (or attachable) to a tube or pipe, such as via a clamp.

The flow detectors described herein (e.g., in FIGS. 14, and 20-33E) may have a means to calibrate the detected sound to a flow rate, such flow rate measured by a preconfigured and calibrated detector system. The detector may have adjustments or inputs of calibration data or settings.

In some cases, the acoustic flow sensors described herein (e.g., in FIGS. 14, and 20-33E) may also measure other parameters of a flowing gas, such as pressure and/or temperature. In some cases, the acoustic flow sensors described herein (e.g., in FIGS. 14, and 20-33E) may work in conjunction with another one or more sensors that measure other parameters of a flowing gas, such as pressure and/or temperature. A processor (e.g., that is part of the control system) may convert the detected sound (e.g., intensity and/or frequency) and another detected parameter (e.g., temperature and/or pressure) to a flow rate of the gas. In some cases, a measured flow rate of a gas and another detected parameter (e.g., temperature and/or pressure) can be used by the control system to convert a gas flow rate to an amount of gas (e.g., air, or oxygen) moving past (or through) the sensor (or moving within a tube). In some cases, the total amount of gas moving through the sensor system may be calculated from inputs from independent flow, pressure, and temperature sensors.

Figure 34A:
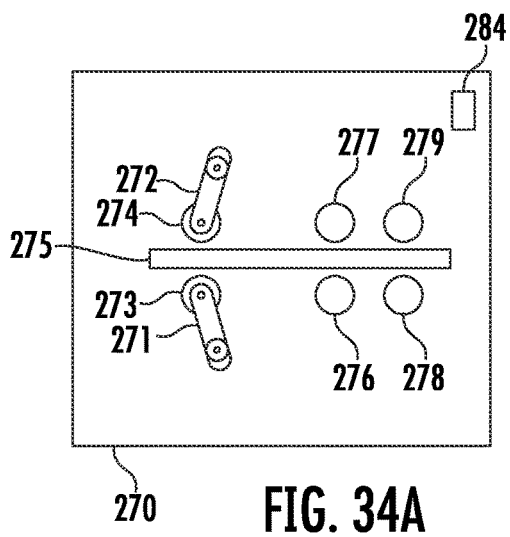
FIGS. 34A-34C are simplified schematics of an example of a ventilator system with a removable airway, in accordance with some embodiments.
Figure 34B:
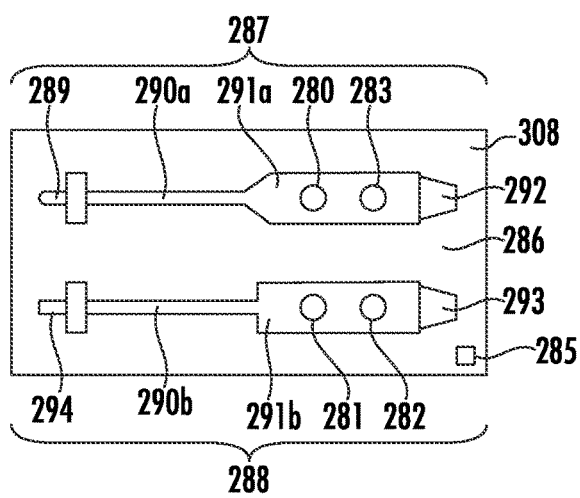
Figure 34C:
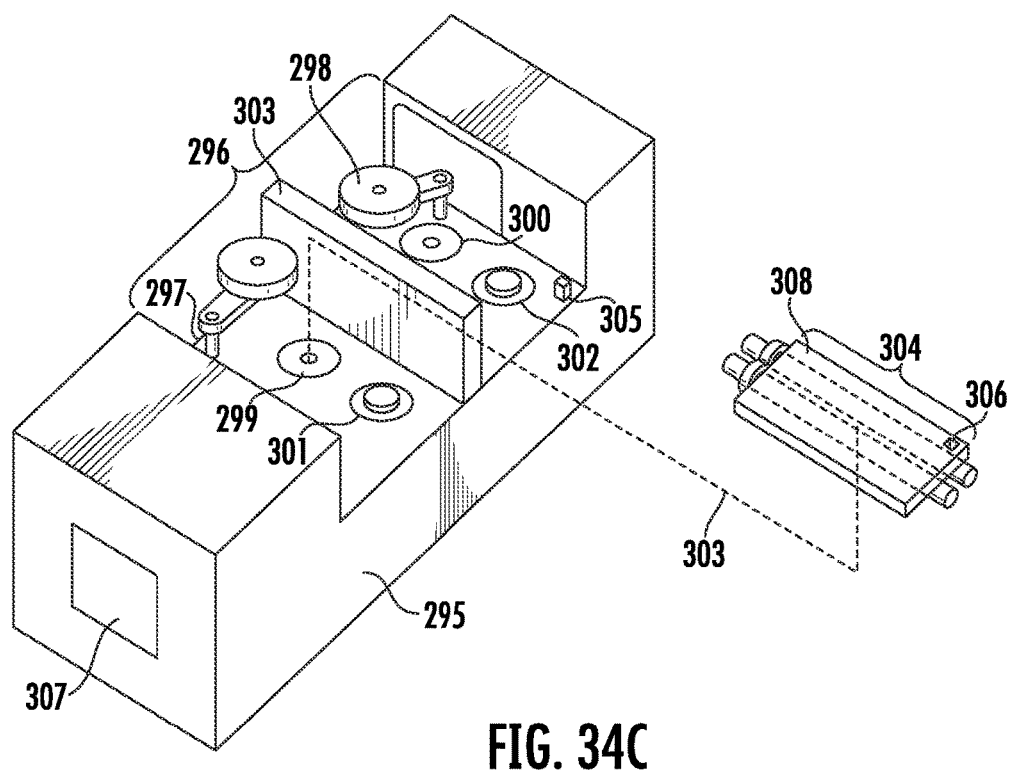

FIGS. 34A-34C are simplified schematics of an example of a ventilator system with a removable airway, in accordance with some embodiments. FIG. 34A is a top view of a ventilator base unit section 270 (e.g., base unit 180 in FIG. 19) into which a removable unit may be inserted. FIG. 34B is a bottom view of a removable unit 286 (e.g., removable system (or removable airway) 179 in FIG. 19) that can be inserted onto the base unit section 270 in FIG. 34A. FIG. 34C is an isometric view of both the base unit 295 (e.g., containing portion of base unit 270 in FIG. 34A) and the removable unit 304 (e.g., 286 in FIG. 34A). The control of flow within the removable unit 286 (or 304) is via pinch valves, where the pinch valves include a roller 273 or 274 (or other means such as a plunger), where the roller 273 or 274 (or plunger, or other means) is configured to compress a flexible tube of the removable unit 286 (or 304). The pinch valve may have multiple movable elements which may in combination compress a tube, such as two opposing elements with a tube in between where both elements move towards each other to close a gap between them thus compressing the tube, such as in a scissor mechanism.

In some embodiments, the rate of flow within the removable unit 286 (or 304) may be controlled by controlling how much a pinch valve compresses a tube of the removable unit 286 (or 304), and how much of a constriction is formed within the tube. The tube may be closed off with sufficient pressure from the pinch valve to constrict the tube completely. The flow sensors may be positioned downstream of the valve on the inhale side, and upstream of the valve on the exhale side. The removable unit 286 (or 304) may have two airways, one for inhale and one for exhale, that may be linear or straight tubes. At the ends of the tubes may be connectors for gases. The tubes may be mounted on a plate or other means that keeps the tubes in a fixed relative position. The removable unit 286 (or 304) may fit into the portion of the base unit 270 (or the base unit 295) in a predetermined location with only one possible orientation with suitable mating portions (e.g., pins, slats, holes, slots, structures that fit together in the manner of puzzle pieces) on the portion of the base unit 270 (or the base unit 295) and removable unit 286 (or 304). The removable unit 286 (or 304) may also lock or snap into place, or have a clasp that is automatically or manually engaged when the disposable is manually installed in the portion of the base unit 270 (or the base unit 295). The air inlets and outlets of removable unit 286 (or 304) may be tapered to mate with standard ventilator airway components, such as a patient circuit (i.e., the tubes that connect a ventilator to the trachea tube or mask of a patient), or filters. A connector on the inhale side of the removable unit 286 (or 304) may be of a type to connect to an air supply, such as a hospital air supply. The valves may have a roller that can press on a tube of removable unit 286 (or 304), and a rib (e.g., between two valves) to back the tube when it is pressed on. The flow and/or pressure sensors (or first portions thereof) may be mounted in the portion of the base unit 270 (or the base unit 295) facing upwards so as to measure flow within removable unit 286 (or 304), and/or so as to mate with second portions of the sensors (e.g., diaphragms) on the removable unit 286 (or 304).

While other types of sensors and configurations of valves are possible, as described above, FIGS. 34A-34C show one example ventilator system. A portion of a base unit 270 has two rotatable arms 271 and 272. On the ends of arms 271 and 272, extends rollers 273 and 274. Between rollers 273 and 274 is a wall or rib 275 (that may be non-flexible, or have limited flexibility), such that a tube of the removable unit 286 when placed between the roller and the rib may be compressed. Each valve contains a rotatable arm 271 or 272, a roller 273 or 274, and the wall or rib 275. The valves shown in FIGS. 34A-34C may be configured to variably adjust the flow of gas through the valve (i.e., through tube 290a or 290b passing through the valve, or through a compressible section of a tube 290a or 290b passing through the valve), as described herein. For example, each rotatable arm 271 and 272 may have a plurality of positions configured to compress tube 290a or 290b (or to compress a compressible section of tube 290a or 290b) by varying amounts. The portion of the base unit 270 also contains microphones 276 and 277, that are configured to mate with the associated components 280 and 281 of the removable unit 286 (shown in FIG. 34B) to form a flow sensor. The portion of the base unit 270 also contains force sensors (e.g., load cells) 278 and 279. The force sensors 278 and 279 are configured to mate with the congruent parts (e.g., compliant regions) 282 and 283 of the removable unit 286 (shown in FIG. 34B) to form a pressure sensor to detect the pressure in the airway of the removable unit 286. In some cases, the ventilator system in FIGS. 34A-34C may contain one or more blow-off valves that open in response to a maximum pressure being detected in the inhale and/or exhale lines.

The portion of the base unit 270 (or the base unit 295) and the removable unit 286 (or 304) may have a system that aligns the two upon insertion, and also allows insertion only in a particular orientation, such as a square protrusion on the base 284 and a square hole on the disposable 285. Many other lock and key systems are possible. For example, the shape of the plate on the removable unit 286 (or 304) may be such that it fits into the portion of the base unit 270 (or the base unit 295) in a single orientation.

The removable unit 286 (or 304) may include two airways, inhale line or airway 287 and exhale line or airway 288 that are not connected to each other. The inhale line or airway 287 may have a connector 289 to a gas source. Tubes 290a and 290b that are flexible tubes, and may have diameters smaller than the diameter of the patient circuit (e.g., smaller than around 20 mm to 25 mm in diameter), such that a the inner diameter of tubes 290a and 290b are from 2 mm to 6 mm, or smaller than 10 mm Tubes with small diameters (e.g., less than 10 mm), may allow for greater control of the flow within inhale line or airway 287 and exhale line or airway 288, when air from a high-pressure source is used. The tube 290a connects to a section 291a (where section 291a may have a larger diameter than tube 290a). Section 291a may have lower flexibility than tube 290a, and contains the mating portions of the flow sensor (e.g., a diaphragm) 280, and pressure sensor (e.g., a compliant region) 283. In some embodiments, there are no openings around the mating portions of the flow sensor (e.g., a diaphragm) 280, or around the mating portions of the pressure sensor (e.g., a compliant region) 283. Therefore, there is no opening (or port) for air (or air with other matter, such as particles) to escape inhale line or airway 287 and exhale line or airway 288 of the removable unit 286 other than through the dedicated ports 289, 294, 292, and 293. The air within inhale line or airway 287 can exit through a connector portion (or port) 292, which may be tapered to match a tube of a patient circuit. The exhale line or airway 288 has a similar inlet (or port) 293, which also may be tapered to match a tube of a patient circuit (although, in some cases port 293 may be of a different dimension than port 292 in the inhale line to prevent misconnecting inhale and exhale patient circuit lines (or tubes)). The exhale airway 288 may have an exit connector (or port) 294 that may be tapered to mate with other ventilator components. For example, port 294 may connect to a filter or other air cleaning means, such as thermal or UV sterilizers (e.g., to filter out particles or infectious material before they are expelled to the atmosphere). The inner diameter of the components of exhale line or airway 288 may be similar to that of a patient circuit exhale line (and/or an endotracheal tube) to allow for minimal restriction of exhale flow between the patient circuit exhale line and the ventilator exhale line or airway 288. Thus the inner diameter of section 291a may be between 15 mm and 25 mm. The inhale line or airway 287 may be of any advantageous diameter to achieve control of flow and pressure.

FIG. 34C shows base unit 295 having a region 296 (which is the same as, or similar to, portion of base unit 270 in FIG. 34A) that accepts a removable airway unit 304 (which is the same as, or similar to, removable unit 286 in FIG. 34B). Region 296 includes components of adjustable pinch valves 297 and 298 with fixed means (e.g., plate) 303, microphones 299 and 300, and force sensors 301 and 302. Valve 297 and/or 298 may be configured to variably adjust the flow of gas through the valve (i.e., through a tube passing through the valve, or through a compressible section of a tube passing through the valve), as described herein. The removable airway 304 is inserted generally along a path 303 into the base unit region 296. Alignment means 305 and 306 are shown as a protruding prism 305 that mates with hole 306. The base unit may have a means of human interaction region 307, for example a touch screen, a display, a control panel, or other user interface (e.g., with buttons, knobs, sliders etc.). The ventilator system shown in FIG. 34C may also have wireless communication, such as via WiFi or Bluetooth, and connect to a human interaction interface on a separate device (e.g., a remote control, computer, smartphone, or tablet) that may view the status of the ventilator and/or control it.

The region 296 is shown on the top of the base unit 295 in FIG. 34C, however, in other embodiments, region 296 may be on a different surface or orientation of a ventilator base unit, such as at the back, or on the sides, or underneath. The shape of the tubes in the removable unit 286 or 304 may be straight as shown in FIGS. 34B and 34C, or may have right angles, or have other angles, or be curved. In some embodiments, the connectors may be at right angles to the plane 308 (on the top of the removable unit 304) such that the removable unit 304 may be inserted in a region the base unit (smaller or larger in area than the removable unit 304), such that the tubes of the removable unit 304 can be connected (e.g., to an air supply, a patient circuit, and/or a filter) in a perpendicular direction from the base unit 295.

The ventilator systems shown in FIGS. 34A-34C may incorporate additional valves and sensors, or may have fewer valves and sensors than shown in the figures.

For example, an additional pressure sensor may be disposed upstream of the inhale valve to measure the pressure in the inhale line or airway 287 when the valve is closed. This may help to adjust the valve for a predetermined flow when it is opened, especially when the pressure upstream of the valve changes when the valve is closed, so that the position the valve had been in to achieve a set flow will now be different when the valve is open. Using the pressure in the upstream line may help to predetermine a setting of the valve on the subsequent cycle. It may, for example, yield a starting point for the valve position that will be closer to a valve position setting that achieves the desired flow, as the valve may be in closed-loop control with the flow sensor. An additional air inlet (or port) to inhale line or airway 287 may be included such that there is one inlet for one for oxygen and one inlet for air or nitrogen. Thus, the removable unit 286 (or 304) may have a plurality of gas inlets. Additional valves (e.g., pinch valves) and sensors (e.g., oxygen sensors) may be disposed in the system for the purpose of mixing of the gases from multiple gas inlets in the inhale line or airway 287. For example, an optical luminescence type of oxygen sensor could be used, such that oxygen can be sensed without a port that exposes the air within the inhale line or airway 287 to the sensor. For example, the luminous material of an oxygen sensor may be mounted in the inhale line or airway 287 of the removable unit 286 (or 304), and the source and sensor components can be mounted in the base unit 270 (or 295).

A system with fewer sensors than the systems shown in FIGS. 34A-34C may have no sensors on the exhale line. Volume control may be achieved by measuring the inhaled delivered volume (tidal volume) (e.g., using a flow meter in the inhale line), and the exhale valve can be used to maintain PEEP (e.g., using a pressure sensor in the exhale line). PIP (peak inspiratory pressure) may also be controlled by the sensors in the inhale line or airway 287. In this way, a volume may be delivered, and the PEEP controlled, such that as long as the PIP and PEEP are maintained, it may not be necessary to measure the exhaled volume.

In some embodiments, the inhale lines or airways (e.g., 287) may have a constant inflow or air and orifices that allow gas to escape (e.g., at a generally fixed rate). Having a constant inflow of air into the disposable may prevent material getting into the gas supply lines thus keeping them clean. The orifices may be tubes that may be valved by pinching as described above. The tubes may have inner diameters from 0.1 mm to 1 mm, or from 0.01 mm to 0.1 mm, or the tubes may have larger diameters and each tube may contain an orifice with an inner diameter from 0.1 mm to 1 mm, or from 0.01 mm to 0.1 mm. In some cases, such openings in the inhale line or airway 287 are either closed, or when open have a gas flow exiting them. In some cases, these opening tubes may be connected to the exhale exhaust such that some gas is always flowing out the exhaust (from the inhale side) while connected to source gases.

The inhale line or airway 287 may also have a system comprising a region through which the inhale gases (e.g., air, or oxygen mixed with air or nitrogen) flow that is a sterilizing region, such as by UV light or by heat, such as a region including a heated volume with temperatures from 100° C. to 300° C. This region may sterilize incoming gases and any gas or matter that may move upstream into the gas sources.

The flow and pressure control of the ventilator systems shown in FIGS. 34A-34C may be in open-loop or closed-loop control. If a system has a predetermined flow at a predetermined valve position, then open loop control may be effective. More accurate control may be achieved where the valves are continuously adjusted in response to a measured flow, a measured pressure, and/or another measured parameter, where continually means a cycle of measure and adjust and measure and adjust. In some cases, the control system monitors pressure, and valves are opened and closed in response to maximum and minimum pressure limits (e.g., PIP and PEEP thresholds).

The flow sensors of the ventilator systems shown in FIGS. 34A-34C may be affected by the pressure within the inhale and exhale lines or airways 287 and 288. That is, at a certain flow rate, the sensor may read differently at different pressures. A system may be calibrated such that the flow rate determined from a measurement of the flow sensor is converted to a flow rate based on a generally concurrent reading of the pressure (measured using the pressure sensors), such as by using a look up table or predetermined formula.

Figure 35A:
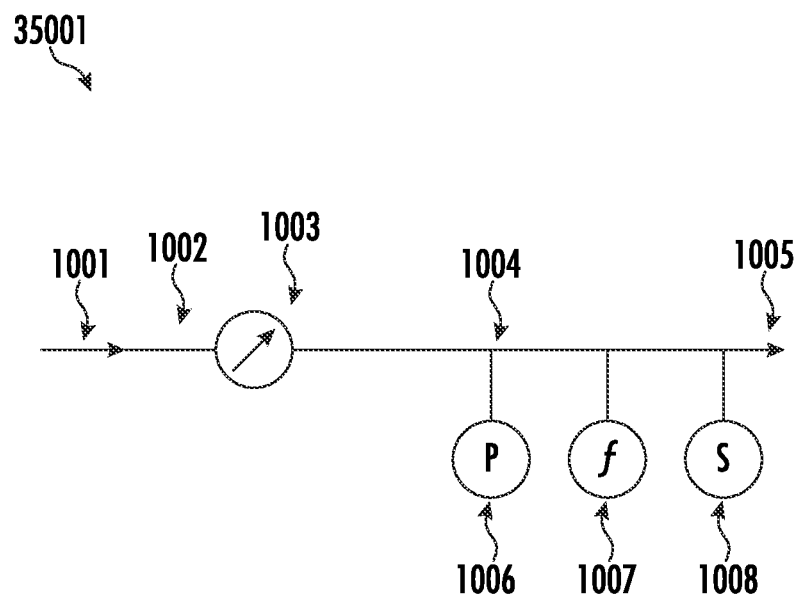
FIGS. 35A-35B are simplified schematics of examples of an inhale line and an exhale line, respectively, of a ventilator system, in accordance with some embodiments.
Figure 35B:
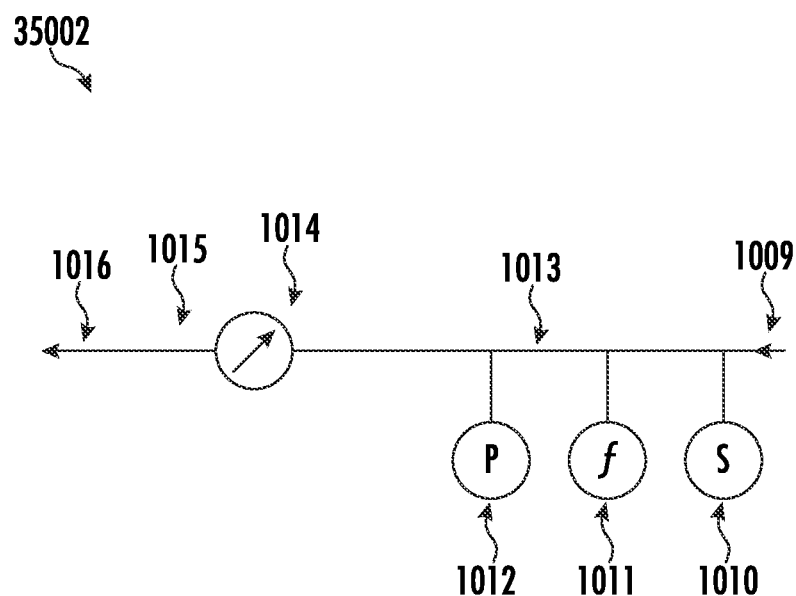

FIGS. 35A-35B are simplified schematics of examples of an inhale line and an exhale line, respectively, of a ventilator system, in accordance with some embodiments. The inhale line 35001 in FIG. 35A and the exhale line 35002 in FIG. 35B, may be the same as or similar to the inhale line or airway 287 and exhale line or airway 288 shown in FIGS. 34A-34C. Air inlet 1001 of inhale line 35002 in FIG. 35A may be coupled to an air source (or to a source of oxygen mixed with other gases), which then passes through a tube 1002 to a variable valve 1003 (e.g., a pinch valve as described herein, for example, in FIGS. 3A-7, and 34A-34C). In some cases, air inlet 1001 is coupled to a gas source (e.g., air, or oxygen mixed with other gases), and the gas source is pressurized (e.g., at about 50 psi). In some cases, the ventilator system may contain a pump or compressor (e.g., in a base unit) to pressurize the gas before it is introduced into air inlet 1001. The air exits variable valve 1003 and enters a manifold (or tube) section 1004. Pressure sensor 1006 (e.g., a pressure sensor shown in FIGS. 21A-23B), flow sensor 1007 (e.g., an acoustic flow sensor shown in FIGS. 24-33E, and 34A-34C), and other sensors 1008 (such as a temperature sensor) are configured to measure pressure, flow, and other parameters (e.g., temperature) within tube section 1004, as described herein. The tube section 1004 is connected to an air outlet port 1005 to which may be connected an inhalation line of a patient circuit (and/or an endotracheal tube).

FIG. 35B shows an example of an exhale line 35002. An air expiratory line of a patient circuit (and/or an endotracheal tube) that may be connected to port 1009, which is connected to a section of a manifold (or tube) section 1013 with various sensors connected to it. Pressure sensor 1012 (e.g., a pressure sensor shown in FIGS. 21A-23B), flow sensor 1011 (e.g., an acoustic flow sensor shown in FIGS. 24-33E, and 34A-34C), and other sensors 1010 (such as a temperature sensor) are configured to measure pressure, flow, and other parameters (e.g., temperature) within manifold (or tube) section 1013, as described herein. The sensing section of the manifold (or tube) section 1013 is connected to a variable valve 1014 (e.g., a pinch valve as described herein, for example, in FIGS. 3A-7, and 34A-34C) which is connected via a tube 1015 to an exit port 1016. Exit port 1016 may include a filter (e.g., to remove or reduce the concentration of contaminants such as particles and pathogens before air from the exhale line 35002 is expelled into the atmosphere).

In some cases, the ventilator system in FIGS. 35A-35B may contain one or more blow-off valves that open in response to a maximum pressure being detected in the inhale and/or exhale lines 35001 and 35002. The variable valves 1003 and 1014 shown in FIGS. 35A-35B may be configured to variably adjust the flow of gas through the valve (i.e., through tube 1002 or 1015 passing through the valve, or through a compressible section of tube 1002 or 1015 passing through the valve), as described herein.

EXAMPLE METHODS

In some embodiments, a method for using a ventilator system (e.g., ventilator system shown in FIGS. 34A-34C and/or 35A-35B) includes the following steps. An inhale valve (e.g., variable valve 1003 in FIG. 35A) may be opened to allow air (or a mixture of oxygen and other gases) to enter an inhale line (e.g., 35001 in FIG. 35A). In some cases, the inhale line is coupled to a gas source (e.g., air, or oxygen mixed with other gases), and the gas source is pressurized (e.g., at about 50 psi). In some cases, the ventilator system may contain a pump or compressor to pressurize the gas before it is introduced into the inhale line. The pressure, flow and/or other parameters (e.g., temperature) of the gas within the inhale line may be monitored using sensors (e.g., sensors 1006, 1007 and 1008 in FIG. 35A). The inhale valve (e.g., variable valve 1003 in FIG. 35A) may be controlled by a control system, and the control system may be configured to receive measurement information from the sensors. The inhale valve (e.g., variable valve 1003 in FIG. 35A) may be opened to a predetermined position, or may be controlled in a closed-loop feedback based on sensor measurements. The inhale valve (e.g., variable valve 1003 in FIG. 35A) may be configured to variably adjust the flow of gas through the valve (i.e., through a tube passing through the valve, or through a compressible section of a tube passing through the valve). After the inhale valve is opened, air from the inhale line may be provided to a patient coupled to the inhale valve (e.g., via a patient circuit, and/or endotracheal tube), and the patient's lung(s) may fill with the air.

As air is being provided to the patient, the pressure in the inhale line may be monitored, and once a maximum PIP threshold is reached, then the control system may close the inhale valve and open an exhale valve (e.g., variable valve 1014 in FIG. 35B) on an exhale line (e.g., 35002 in FIG. 35B). After the exhale valve is opened and the inhale valve is closed, then air may flow from the patient's lung(s) into the exhale line, and out of an exit port (e.g., 1016 in FIG. 35B). While air is flowing from the patient to the exhale line (and out the exit port) the pressure in the exhale line may be monitored, and once a minimum PEEP threshold is reached, then the control system may close the exhale valve and open the inhale valve on the inhale line. The exhale valve (e.g., variable valve 1014 in FIG. 35B) may be configured to variably adjust the flow of gas through the valve (i.e., through a tube passing through the valve, or through a compressible section of a tube passing through the valve). After the exhale valve is closed and the inhale valve is opened, then air from the inhale line may again be provided to a patient, and the method can continue as described above. The inhale/exhale cycle described above may then be repeated many times (e.g., about 20 times per minute, for hours or days, or weeks).

In some cases of the above method, the control system may have one or more predetermined user-settable or fixed delays, such as 1 second or less to 3 seconds or more, between any of the steps of the method. The delay may be zero in some cases. For example, after the PIP threshold is detected, and after the inhale valve is closed, there may be a delay before the exhale valve is opened.

In alternative embodiments of the method above, flow may be used to control the valves instead of, or in addition to, the pressure control method described above. In some cases, temperature, flow and pressure, may all be measured and used to control the valves, instead of, or in addition to, the pressure control method described above. For example, one or more of the flow and/or pressure and/or temperature sensors described herein, may measure parameters of a flowing gas, such as flow rate, pressure and/or temperature. A processor (e.g., that is part of the control system) may convert the parameters (e.g., flow rate, temperature, and/or pressure) to a flow rate and/or pressure of the gas, and the control system can then use the converted parameters to control components (e.g., valves) of the ventilator system. In some cases, a measured flow rate of a gas and another detected parameter (e.g., temperature and/or pressure) can be used by the control system to convert a gas flow rate to an amount of gas (e.g., air, or oxygen) moving past (or through) the sensor (or moving within a tube). In some cases, the total amount of gas moving through the sensor system may be calculated from inputs from independent flow, pressure, and temperature sensors. The valves of the systems operating in the above modes may also be configured to variably adjust the flow of gas through each of the valves.

In some embodiments, a method for using a ventilator system (e.g., ventilator system shown in FIGS. 1-2 and 15-16) includes the following steps. In a tidal volume inhalation control mode, a first valve (e.g., valve 5 in FIG. 1) on an inhale line is opened and a second valve (e.g., valve 9 in FIG. 1) on an inhale line is closed. The first valve may be configured to variably adjust the flow of gas through the valve. A first bellows (e.g., bellows 7 in FIG. 1) positioned downstream of the first valve and upstream of the second valve inflates (e.g., due to the air pressure from a pressurized source) to a pre-determined volume, such as 500 cc, from 50 cc to 1000 cc, or from less than 50 cc to more than 1000 cc. When the predetermined volume has been reached, the control system closes the first valve and opens the second valve. Valves (e.g., 18 and 23 in FIG. 2) on an exhale line may be open or closed during inflation of the first bellows. When the second valve opens, gas begins to inflate the lung(s) of a patient, and pressure builds in a first pressure-limiting subsystem (e.g., pressure-limiting and pressure-detection subsystem 11 in FIG. 1) coupled to the inhale line (e.g., downstream of the second valve). When pressure in the first pressure-limiting subsystem reaches a predetermined value, or PIP (e.g., about 30 cmH$_2$O, about 40 cmH$_2$O, or from 15 cmH$_2$O to 45 cmH$_2$O, or from less than 15 cmH$_2$O to more than 45 cmH$_2$O), then the second valve is closed by the control system, completing an inhale cycle. The first valve may then be opened to fill the first bellows to be ready for the next inhale cycle of this mode.

When the second valve closes, the exhale cycle of this mode may commence. The control system may have a predetermined user-settable or fixed delay, such as 1 second or less to 3 seconds or more, such that valve 18 may open after the delay has passed. The delay may be zero in some cases. When a third valve (e.g., valve 18 in FIG. 2) on an exhale line opens, gas begins to pass from the lungs into a tube (e.g., tube 19*a* in FIG. 2) of the exhale line. In one mode, a fourth valve (e.g., valve 23 in FIG. 2) on the exhale line may be closed during a first portion of the exhale cycle. A subsystem (e.g., subsystem 20 in FIG. 2) maintains the pressure at or above a preset value (e.g., about 5 cmH$_2$O, or from 2 cmH$_2$O to 15 cmH$_2$O, or from less than 2 cmH$_2$O to more than 15 cmH$_2$O), and a second bellows (e.g., bellows 21 in FIG. 2) on the exhale line fills with exhaled gas from the patient. Gas may also flow through a flow sensor (e.g., flow sensor subsystem 30 in FIG. 2) on the exhale line. The end of the first portion of the exhale cycle may be determined either by the second bellows reaching a predetermined volume, or by the flow sensor on the exhale line detecting a pre-determined low level of flow, such as no flow, or by the pressure sensor reaching a preset minimum value (PEEP). When any of these end-of-exhale conditions is reached, the control system closes the third valve and opens the fourth valve, initiating a second portion of the exhale cycle. In the second portion of the exhale cycle, gas in the second bellows is emitted through an exit port (e.g., exit port 25 in FIG. 2) to the atmosphere, thereby completing the exhale cycle. The second, third and/or fourth valves may also be configured to variably adjust the flow of gas through each of the valves. After the exhale cycle is complete, there may include a delay (e.g., of 1 second or less and up to 3 seconds or more) before repeating the inhale cycle, as described above.

In some embodiments, a method for using a ventilator system (e.g., ventilator system shown in FIGS. 1-2 and 15-16) includes the following steps. In a pressure control mode of operation, the ventilator system uses the PIP, as determined by a preset value of a peek pressure-limiting subsystem (e.g., pressure-limiting and pressure-detection subsystem 11 in FIG. 1), to control the system. In this mode, both valves on the inhale line (e.g., valves 5 and 9 in FIG. 1) are opened simultaneously at the start of an inhale cycle. The lungs of the patient inflate to a pressure that stops increasing due to the action of the pressure-limiting subsystem. When the limiting pressure is reached, the control system receives a signal from pressure-limiting subsystem (e.g., indicating that a PIP has reached a threshold value, e.g., about 30 cmH$_2$O, about 40 cmH$_2$O, or from 15 cmH$_2$O to 45 cmH$_2$O, or from less than 15 cmH$_2$O to more than 45 cmH$_2$O), and the control system closes one or both valves on the inhale line. The exhale cycle is then initiated as described in the method above with respect to the tidal volume inhalation control mode (e.g., with suitable delays). As above, the end of the exhale cycle may be determined via a flow sensor on the exhale line, or the second bellows volume. After the exhale cycle is complete, there may include a delay (e.g., of 1 second or less and up to 3 seconds or more) before repeating the inhale cycle described above. The valves of the systems operating in the above mode may also be configured to variably adjust the flow of gas through each of the valves.

The preceding two modes of operation are commonly referred to as "Mandatory Breathing" mode. Another clinically desirable mode is commonly referred to as "Triggered" or "Spontaneous" breathing mode. In a triggered breathing mode, at the end of an exhale cycle, with the second inhale valve closed and the first inhale valve open, pressure sensor subsystem on the inhale line may be monitored for a negative pressure (e.g., about negative 2 cmH$_2$O, or from negative 4 cmH$_2$O to negative 2 cmH$_2$O, or from less than negative 4 cmH$_2$O to more than negative 2 cmH$_2$O), and a negative pressure threshold may be set to a predetermined value. When the negative pressure threshold in pressure sensor subsystem on the inhale line is reached or the pressure is pressure sensor subsystem on the inhale line more negative than the threshold, then the control system may open the second valve on the inhale line. The pressure-limiting subsystem on the inhale line may be set to a predetermined value (e.g., about 10 cmH$_2$O, or from 4 cmH$_2$O to 20 cmH$_2$O, or from less than 4 cmH$_2$O to more than 20 cmH$_2$O), such that the breathing is assisted by a background pressure above atmospheric pressure. The end of the inhale cycle in this triggered breathing mode may be determined by the flow sensor subsystem on the inhale line detecting a preset low level of flow (e.g., about 3 liters per minute (lpm), or from 1 lpm to 10 lpm). In this mode, the exhale cycle may be the same as in the method described above for the mandatory breathing modes, and the exhale cycle end may be determined by volume exhaled or by flow rate. Additionally, after the exhale cycle is complete, there may include a delay (e.g., of 1 second or less and up to 3 seconds or more) before repeating the inhale cycle for the triggered breathing mode (as described above). The valves of the systems operating in the above mode may also be configured to variably adjust the flow of gas through each of the valves.

In some embodiments, a method of detecting a flowing gas using sound includes the following steps. A gas (or gaseous mixture including a gas and other matter, such as solid and/or liquid particles) flows through a tube, where the tube can be any shape (e.g., the tube may have an approximately cylindrical volume, a volume with an approximately square or rectangular cross-section, a volume with a semi-circular cross-section, or any other geometry). The gas generates sound as it flows through the tube. The sound is detected by a microphone that is positioned either inside of the tube or outside of the tube. The intensity and/or frequency of the sound is processed to convert the intensity and/or frequency of the sound into a gas flow rate.

In some cases of the method described above, the tube contains one or more regions (e.g., diaphragms) that are configured to generate sound. The microphone may be positioned to detect the sound from the diaphragm. In some cases, a cone or other structure may be used to focus (and in some cases amplify) the sound from the regions of the tube onto the microphone.

In some cases of the method described above, the temperature of the flowing gas may also be measured, and the intensity and/or frequency of the sound, and the temperature of the flowing gas, is processed to convert the intensity and/or frequency of the sound, and the temperature of the flowing gas, into a gas flow rate.

In some cases of the method above, the tube may contain one or more sound-generating structures (e.g., as shown in FIG. 29, or 266a-e as shown in FIGS. 33A-33C).

In some cases of the method above, two or more microphones may be used to detect the sound from the tube and/or the sound-generating structures.

In some cases of the method above, sound-generating structures and microphones may be configured to determine a flow direction of the flowing gas within the tube.

In some cases of the above method, insulation may be arranged to insulate the tube and/or the microphone from ambient noise (i.e., sounds that are not generated by the flowing gas).

In some cases of the method above, the frequency spectrum of the sound is analyzed (e.g., by a processor of the control system) and converted into a gas flow rate (e.g., as described above with respect to FIG. 30). For example, one or more sound-generating structures (e.g., an orifice, a whistle, a reed, or other sound-generating structure) may preferentially generate a range of frequencies when gas flows past (or over, or through) the sound-generating structure, and the frequency spectrum of the generated sound can be analyzed to determine the intensity of the sound within that frequency range. Such a method may advantageously increase the signal-to-noise ratio of the measurement.

Embodiments of the disclosed invention have been referenced in detail, and one or more examples of the disclosed invention have also been illustrated in the accompanying figures. Each of the embodiments and examples herein have been provided to explain the present technology, not as limitations of the present technology. Furthermore, while particular embodiments of the invention have been described in detail, it will be appreciated that alterations to, variations of, and equivalents to these embodiments may be readily conceived of by those skilled in the art, upon attaining an understanding of the foregoing. For instance, features illustrated or described with respect to one embodiment may be used with another embodiment to yield an additional embodiment. It is intended that the present subject matter covers all such modifications and variations within the scope of the appended claims and their equivalents. Those of ordinary skill in the art may practice these and other modifications and variations to the present invention without departing from the scope of the present invention, which is more particularly set forth in the appended claims. Furthermore, the foregoing description is by way of example only, and is not intended to limit the invention, as will be appreciated by those of ordinary skill in the art.

What is claimed is:

1. A ventilator system, comprising:
   a removable airway comprising:
      an air inlet port;
      a patient inhalation port;
      an air exhaust port;
      a patient exhalation port;
      a first portion of a pressure sensor; and
      a first portion of a flow sensor; and
   a base unit comprising:
      two pinch valves;
      a second portion of the pressure sensor; and
      a second portion of the flow sensor,
   wherein air enters the removable airway through the air inlet port,
   wherein air is exhausted from the removable airway through the air exhaust port,
   wherein air leaves the removable airway through the patient inhalation port,
   wherein air enters the removable airway through the patient exhalation port,
   wherein the removable airway does not comprise any openings other than the air inlet port, the air exhaust port, the patient inhalation port, and the patient exhalation port, and
   wherein air inside the removable airway does not contact any part of the base unit without first exiting the air exhaust port.

2. The ventilator system of claim 1, wherein the pinch valves are each configured to variably adjust the flow of gas through the removable airway.

3. The ventilator system of claim 2, wherein the pinch valves each comprise a valve body, an actuator, a moveable element, and a fixed element, wherein the removable airway passes between the fixed element and the moveable element.

4. The ventilator system of claim 3, wherein the moveable element comprises a roller coupled to a rotatable arm.

5. The ventilator system of claim 1, wherein the first portion of the flow sensor comprises a diaphragm, and the second portion of the flow sensor comprises a microphone configured to measure a sound emitted from the diaphragm.

6. The ventilator system of claim 5, wherein the microphone is located within a cone configured to amplify the sound emitted from the diaphragm.

7. The ventilator system of claim 5, wherein the microphone comprises a gain that is adjustable in real time in response to changes in amplitude of the sound emitted from the diaphragm.

8. The ventilator system of claim 5, wherein the first portion, the second portion, or both the first and second portions, comprise one or more sound insulation elements configured to reduce the intensity of ambient sounds that are not being emitted from the diaphragm from reaching the microphone.

9. The ventilator system of claim 5, wherein the first portion of the flow sensor further comprises a structure located within the removable airway, wherein the structure is configured to generate sound emitted from the structure when flowing air interacts with the structure.

10. The ventilator system of claim 9, wherein the structure is configured to generate sound at frequencies from 100 Hz to 20 kHz.

11. The ventilator system of claim 9, wherein the structure comprises a reed or a whistle.

12. The ventilator system of claim 9, wherein the structure comprises an orifice through which the air within the removable airway must pass through when flowing, wherein the orifice is narrower than an adjacent downstream region of the removable airway.

13. The ventilator system of claim 1, wherein the two valves each comprise a valve position configured to release the removable airway for removal from the base unit.

14. The ventilator system of claim 1, wherein the first and second portions of the pressure sensor are configured to allow removal of the removable airway from the base unit, and the first and second portions of the flow sensor are configured to allow removal of the removable airway from the base unit.

15. The ventilator system of claim 1, wherein the first portion of the pressure sensor comprises a compliant region, and the second portion of the pressure sensor comprises a means of measuring a change of the compliant region resulting from a pressure change within the removable airway.

16. The ventilator system of claim 1, wherein the first portion of the pressure sensor comprises a compliant region, and the second portion of the pressure sensor comprises an optical measurement system, an electrical measurement system, a mechanical measurement system, a system configured to detect a change in the magnitude or position of light reflected from the compliant region, a system configured to measure a change in capacitance between an electrically conductive portion of the distorted region and a second electrically conductive surface, or a system with a strain gauge configured to measure a change in the distorted region.

17. The ventilator system of claim 1, wherein the first portion of the pressure sensor comprises a compliant region, and the second portion of the pressure sensor comprises a means of measuring a force on the compliant region.

18. The ventilator system of claim 1, wherein the first portion of the pressure sensor comprises a compliant region, and the second portion of the pressure sensor comprises a load cell configured to measure a force on the compliant region.

19. A ventilator system, comprising:
a removable airway comprising:
four ports comprising an air supply port, an air exhaust port, a patient inhalation port, and a patient exhalation port;
a first portion of a first pressure sensor comprising a compliant region; and
a first portion of a first flow sensor comprising a diaphragm; and
a base unit comprising:
two pinch valves, each pinch valve comprising a valve body, an actuator, a moveable element, and a fixed element, wherein a compressible section of the removable airway passes between the fixed element and the moveable element;
a second portion of the first pressure sensor comprising a load cell configured to measure a force on the compliant region; and
a second portion of the first flow sensor comprising a microphone configured to measure a sound emitted from the diaphragm,
wherein the removable airway does not comprise any openings other than the four ports, and
wherein air inside the removable airway does not contact any part of the base unit.

20. The ventilator system of claim 19, wherein:
the removable airway further comprises:
an inhale manifold comprising:
the air supply port;
the patient inhalation port;
the first portion of the first pressure sensor; and
the first portion of the first flow sensor;
an exhale manifold comprising:
the air exhaust port;
the patient exhalation port;
a first portion of a second pressure sensor; and
a first portion of a second flow sensor; and
the base unit further comprises:
a first and a second pinch valve configured to limit flow in the inhale manifold, wherein the moveable element of each of the first and second pinch valves comprise a roller coupled to a rotatable arm;
a third and a fourth pinch valve configured to limit flow in the exhale manifold, wherein the moveable element of each of the third and fourth pinch valves comprise a roller coupled to a rotatable arm;
the second portion of the first pressure sensor;
the second portion of the first flow sensor;
a second portion of the second pressure sensor; and
a second portion of the second flow sensor.

* * * * *